(12) United States Patent
Katayama et al.

(10) Patent No.: US 11,701,498 B2
(45) Date of Patent: Jul. 18, 2023

(54) GUIDE WIRE GRIPPING UNIT

(71) Applicant: OLYMPUS CORPORATION, Hachioji (JP)

(72) Inventors: Tomofumi Katayama, Tokyo (JP); Kunihide Kaji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1002 days.

(21) Appl. No.: 16/544,987

(22) Filed: Aug. 20, 2019

(65) Prior Publication Data
US 2019/0365206 A1    Dec. 5, 2019

Related U.S. Application Data

(63) Continuation of application No. PCT/JP2017/009736, filed on Mar. 10, 2017.

(51) Int. Cl.
*A61M 25/09* (2006.01)
*A61B 17/22* (2006.01)
*A61B 17/00* (2006.01)

(52) U.S. Cl.
CPC . *A61M 25/09041* (2013.01); *A61B 17/22031* (2013.01); *A61B 2017/00269* (2013.01); *A61B 2017/00296* (2013.01)

(58) Field of Classification Search
CPC ....... A61M 25/09041; A61B 17/22031; A61B 2017/00269; A61B 2017/00296; A61B 1/00137; A61B 1/00133; A61B 2017/0034; A61B 17/3478; A61B 2017/22035; A61B 2017/22049; A61B 1/01
See application file for complete search history.

(56) References Cited

U.S. PATENT DOCUMENTS

| 2004/0039250 A1* | 2/2004 | Tholfsen ............... A61F 2/2412 600/104 |
| 2016/0121083 A1 | 5/2016 | Yokota et al. |
| 2018/0249895 A1* | 9/2018 | Calabrese ............ A61B 1/0011 |

FOREIGN PATENT DOCUMENTS

| EP | 3 009 086 A1 | 4/2016 |
| EP | 3 143 921 A1 | 3/2017 |
| JP | 2011-030764 A | 2/2011 |
| JP | 2015-217016 A | 12/2015 |
| JP | 2016-140630 A | 8/2016 |
| WO | 2014/199759 A1 | 12/2014 |

OTHER PUBLICATIONS

May 16, 2017 International Search Report Issued in International Patent Application No. PCT/JP2017/009736.

* cited by examiner

*Primary Examiner* — Richard G Louis
(74) *Attorney, Agent, or Firm* — Oliff PLC

(57) ABSTRACT

A guide wire gripping device is provided that includes: a sheath; an advanceable and retractable part extending along the longitudinal axis of the sheath; an operation control that moves the advanceable and retractable part along the longitudinal axis; a grasping portion having a contact surface having a peripheral edge surrounded by a distal end, a proximal end, and a pair of side ends; and a support part connected to the advanceable and retractable part and fixed to one of the pair of side ends.

20 Claims, 19 Drawing Sheets

GUIDE WIRE GRIPPING UNIT

TECHNICAL FIELD

The present disclosure relates to a guide wire grasping device.

BACKGROUND

For the treatment and examination of luminal organs of the human body, the introduction of medical instruments into the luminal organs using guidewires is a well-known procedure. If a stenosis or obstruction is present in an opening of the hollow organ, the guide wire itself may not be able to be inserted into the luminal organ. For example, when a duodenal papilla is tightly closed, it is difficult to insert the guide wire into a desired luminal organ, such as the bile duct or pancreatic duct, via the duodenal papilla.

A procedure referred to as a rendezvous method may be performed in such a case. In the rendezvous method, a guide wire introduced from a site other than the duodenal papilla into the bile duct or the pancreatic duct is made to protrude from the duodenal papilla, and an end portion of the protruding guide wire is held by a medical instrument. The guide wire protruding from the duodenal papilla is pulled out to the outside of the body via a treatment instrument channel of an endoscope inserted into the duodenum. The guide wire pulled out of the body is used to hold the stent or the like.

For example, Japanese Unexamined Patent Application, First Publication No. 2016-140630 discloses a medical instrument capable of capturing a guide wire protruding from the duodenal papilla. Such a medical instrument has a tubular sheath, a inserted through the sheath, and a distal end provided at the distal end of the wire and extending along the extending direction of the wire. The distal end has a bent portion that is bent into a predetermined shape so that the guide wire can be hooked, Further, for example, as described in U.S. Patent Application, Publication No. 2016/0121083, a method is known in which, when a treatment instrument such as a stent is indwelled by the rendezvous method, a guide wire protruding from the duodenal papilla into the duodenum is drawn back into the bile duct or the pancreatic duct, thereby introducing a medical instrument grasping a wire together with a treatment instrument into the bile duet or pancreatic duct.

Technical Problem

In the method of introducing the medical instrument into the bile duct or the pancreatic duct by pulling back the guide wire as described above, when the medical instrument is inserted into the duodenal papilla, the axis of the medical instrument and the axis of the guide wire grasped by the medical instrument are parallel to each other. This makes it easier for medical instruments to enter the bile duct or the pancreatic duct from the duodenal papilla.

However, in the medical instrument described in Japanese Unexamined Patent Application, First Publication No. 2016-440630, since the guide wire is hooked on the bent portion, a certain angle is formed between the axis line of the medical instrument and the axis line of the guide wire. In such medical instruments, there were cases in which it was difficult to access the bile duct or the pancreatic duct via the duodenal papilla.

SUMMARY

In view of the above circumstances, it is an object of the present disclosure to provide a guide wire grasping device which can be easily introduced into a hollow organ by a rendezvous method.

According to the first aspect of the present disclosure, a guide wire grasping device includes: a sheath having a central axis extending along a longitudinal axis; an advanceable and retractable part extending along the longitudinal axis from a proximal end of the sheath to a distal end of the sheath; an operation control that is provided at a proximal end of the advanceable and retractable part and moves the advanceable and retractable part along the longitudinal axis; a grasping portion having a contact surface having a peripheral edge surrounded by a distal end, a proximal end, and a pair of side ends, the pair of side ends extending between the distal end and the proximal end, the grasping portion extending in a direction along the longitudinal axis; and a support part connected to a distal end of the advanceable and retractable part and fixed to one of the pair of side ends. A gap between the contact surface and an outer peripheral surface of the distal end of the sheath is open at the distal end, the proximal end, and the other of the pair of side ends of the contact surface so that the guide wire is accommodated in the gap from the other of the pair of side ends or the guide wire is released from the gap. The grasping portion is moved to a position facing the outer peripheral surface according to a movement of the advanceable and retractable part and the support part, whereby the guide wire disposed in the gap is grasped between the contact surface and the outer peripheral surface.

According to the second aspect of the present disclosure, in the guide wire grasping device according to the first aspect, the grasping portion may be movable between a first position in which a distance between the contact surface and the distal end of the sheath is larger than an outer diameter of the guide wire and a second position in which a distance between the contact surface and the outer peripheral surface is equal to or smaller than the outer diameter of the guide wire.

According to the third aspect of the present disclosure, in the guide wire grasping device according to the second aspect, the outer peripheral surface may have a flat portion which is a plane parallel to the longitudinal axis. The guide wire may be sandwiched between the contact surface and the flat portion when the grasping portion is in the second position.

According to the fourth aspect of the present disclosure, in the guide wire grasping device according to the second aspect, the outer peripheral surface may have a first concave portion recessed in a cross section extending along the longitudinal axis. The guide wire may be sandwiched between the contact surface and the first concave portion when the grasping portion is in the second position, According to the fifth aspect of the present disclosure, in the guide wire grasping device according to the fourth aspect, the first concave portion may have a bottom portion and a pair of side portions extending from the bottom portion toward the outer peripheral surface. A distance between the pair of side portions may decrease from the distal end to the proximal end of the sheath.

According to the sixth aspect of the present disclosure, in the guide wire grasping device according to the second aspect, the contact surface may have a second concave portion recessed in a cross section extending along the longitudinal axis. The guide wire may be sandwiched between the second concave portion and the outer peripheral surface when the grasping portion is in the second position.

According to the seventh aspect of the present disclosure, in the guide wire grasping device according to the second aspect, the sheath may include: a tubular sheath main body extending along the longitudinal axis; and a tubular distal end provided at a distal end of the sheath main body along the longitudinal axis and having a rigidity higher than that of the sheath main body and constituting a distal end of the sheath. The support part may be attached to the distal end member so as to be rotatable with respect to the distal end member about an axis parallel to a direction substantially orthogonal to the longitudinal axis. The grasping portion may be configured to move between the first position and the second position by the support part rotating relative to the distal end member in accordance with relative movement of the advanceable and retractable part with respect to the sheath.

According to the eighth aspect of the present disclosure, in the guide wire grasping device according to the second aspect, the advanceable and retractable part and the grasping portion may be configured to move relative to the distal end of the sheath along the longitudinal axis. The grasping portion may be configured to move between the first position and the second position by the advanceable and retractable part and the grasping portion moving forward and backward relative to the distal end of the sheath along the longitudinal axis.

According to the above-described guide wire grasping device, it is possible to be easily introduced into a hollow organ by the rendezvous method.

DETAILED DESCRIPTION OF EMBODIMENTS

Hereinafter, a first embodiment of the present disclosure will be described with reference to FIGS. 1 to 10.

Figure 1:
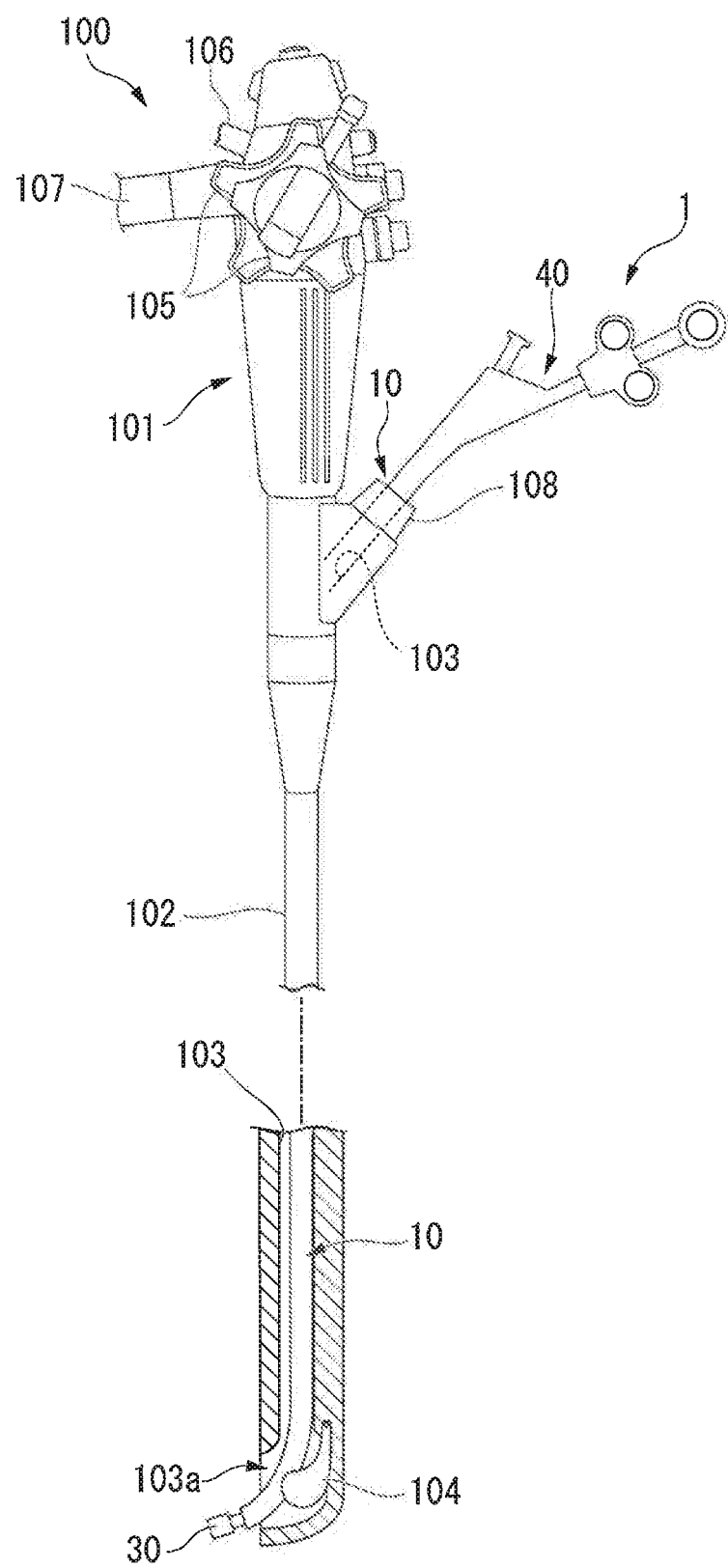
FIG. 1 is an overall view showing a guide wire grasping device and an endoscope used together with the guide wire grasping device according to a first embodiment of the present disclosure.
Figure 2:
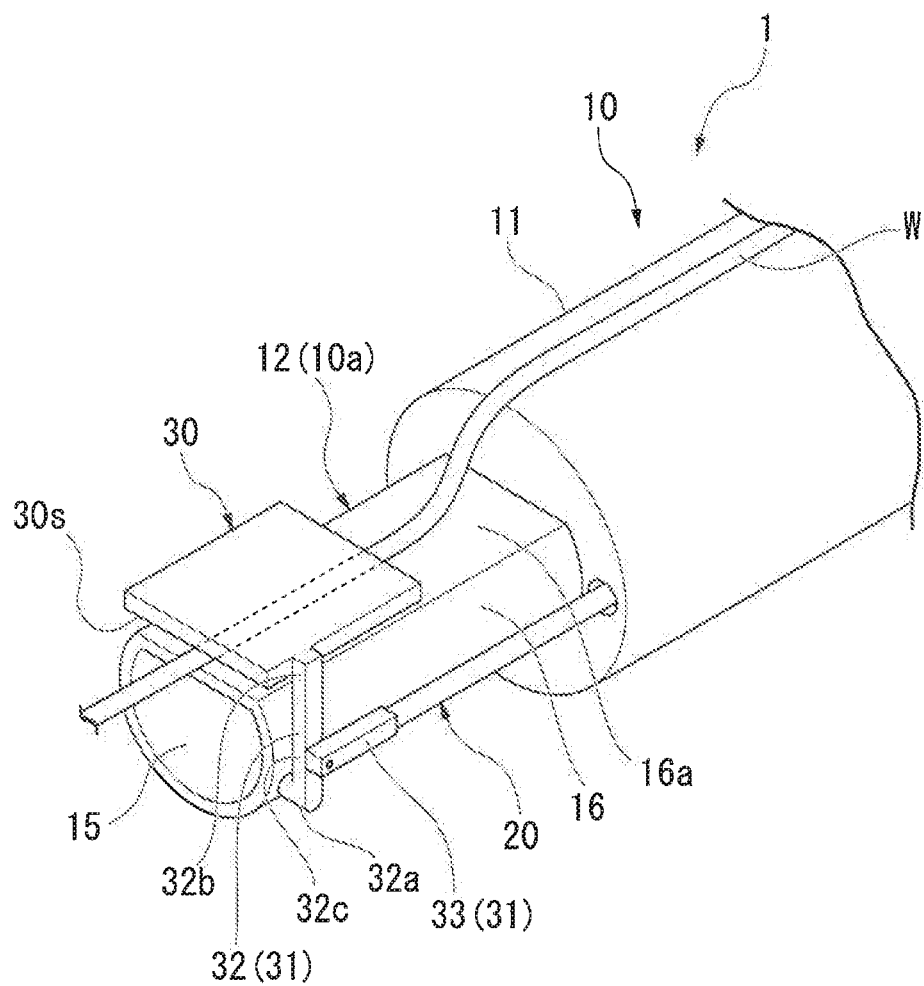
FIG. 2 is a perspective view showing a distal end side of the guide wire grasping device.
Figure 3:
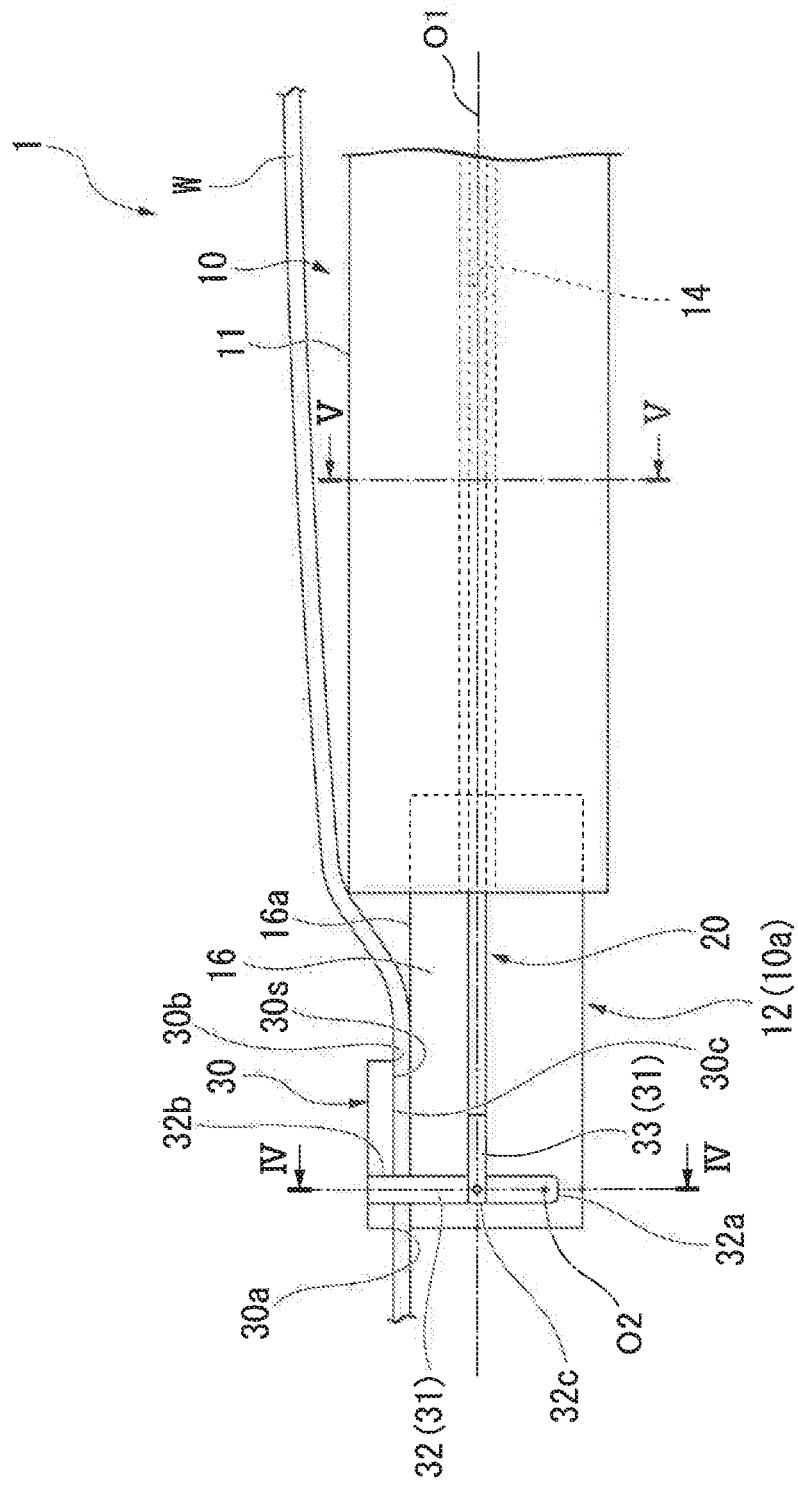
FIG. 3 is a right side view showing the distal end side of the guide wire grasping device.
Figure 4:
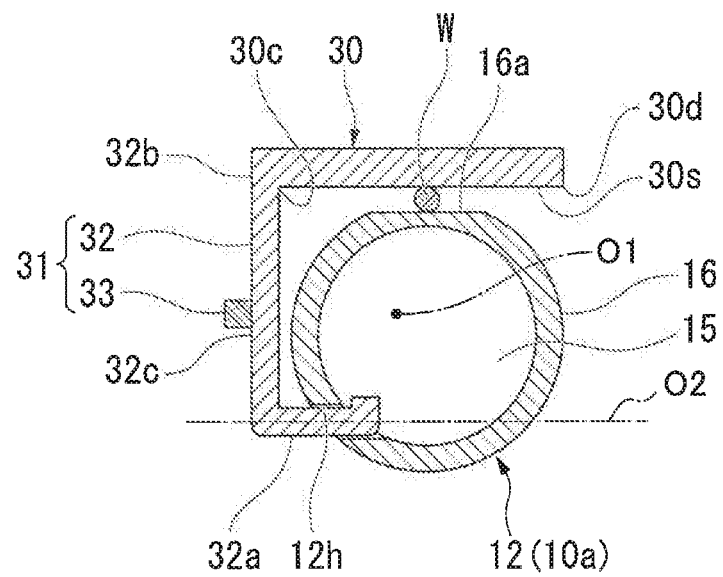
FIG. 4 is a cross-sectional view taken along line IV-IV of FIG. 3.
Figure 5:
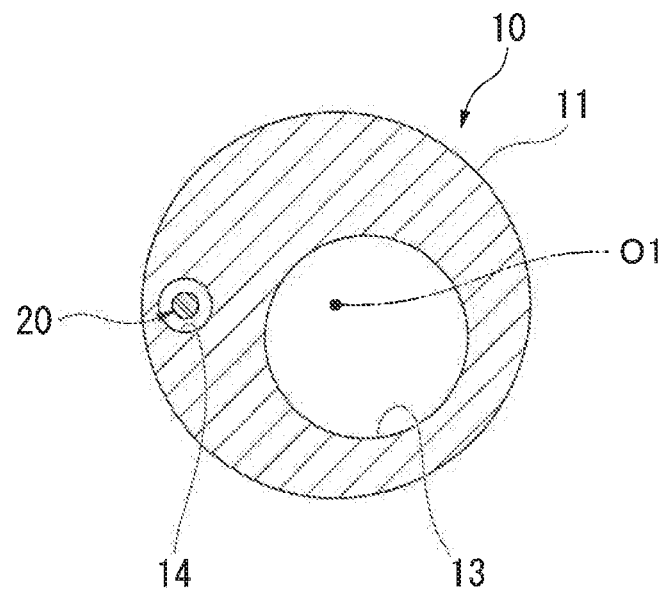
FIG. 5 is a cross-sectional view taken along line V-V in FIG. 3.
Figure 6:
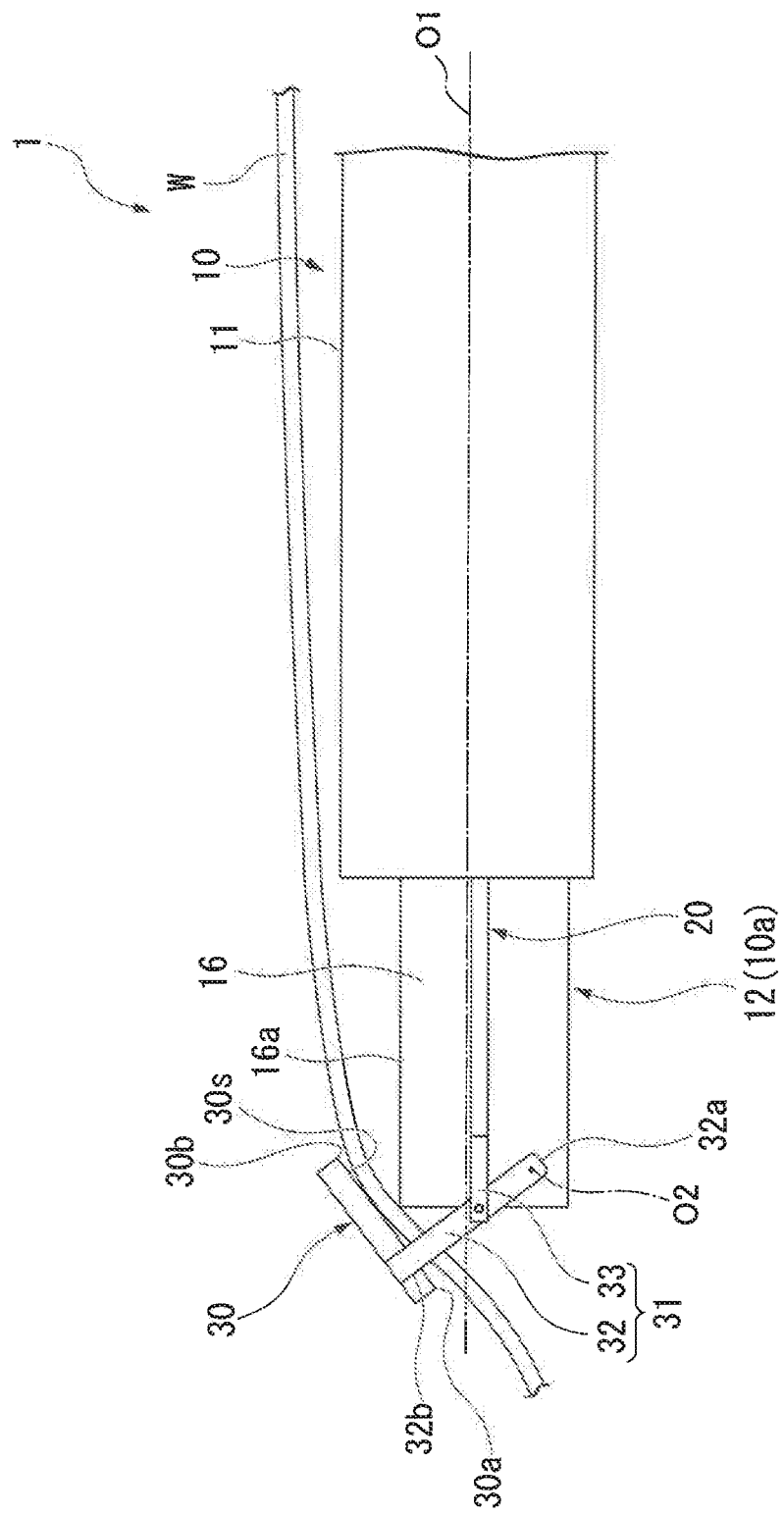
FIG. 6 is a view showing an operation of a grasping member (grasping portion) of the guide wire grasping device.
Figure 7:
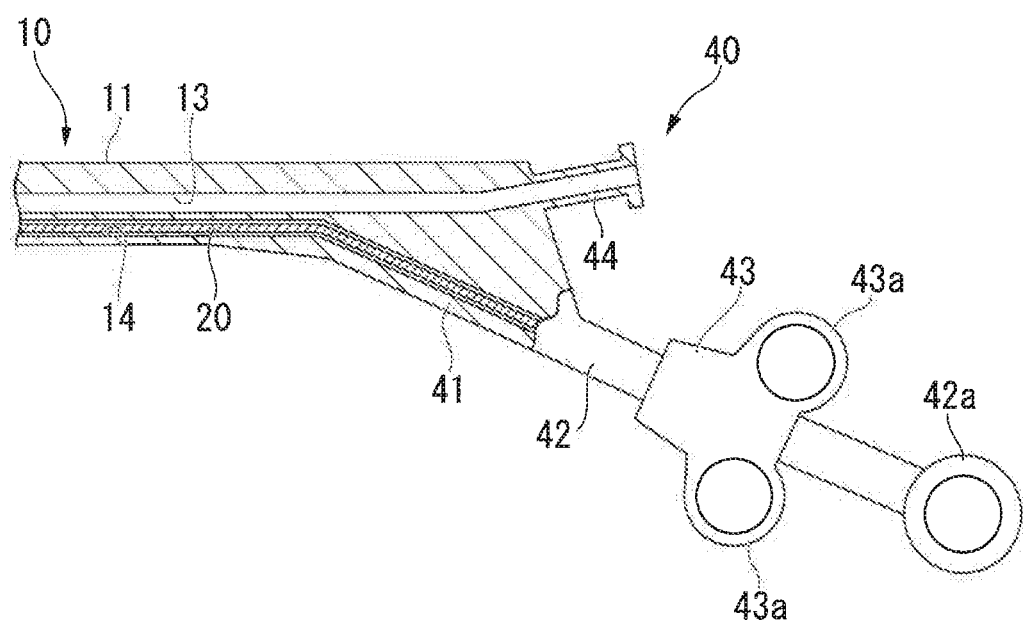
FIG. 7 is a partially broken view of a proximal end side of the guide wire grasping device.

FIG. 1 is an overall view showing a guide wire grasping device 1 and an endoscope 100 used together with the guide wire grasping device 1 according to this embodiment. FIG. 2 is a perspective view showing a distal end side of the guide wire grasping device 1. FIG. 3 is a right side view showing the distal end side of the guide wire grasping device 1. FIG. 4 is a cross-sectional view taken along the line IV-IV of FIG. 3. FIG. 5 is a cross-sectional view taken along the line V-V of FIG. 3. FIG. 6 is a view showing an operation of a grasping member (grasping portion) 30 of the guide wire grasping device 1. FIG. 7 is a partially broken view of a proximal end side of the guide wire grasping device 1.

First, the endoscope 100 used together with the guide wire grasping device 1 will be described. The configuration of the endoscope 100 is not particularly limited, and the endoscope 100 is, for example, a known side-view type endoscope as shown in FIG. 1. The endoscope 100 has an operation part 101 operated by a user and an insertion part 102 extending from the operation part 101. The insertion part 102 is insertable into the body and is formed to be elongated having flexibility. In the insertion part 102, a channel 103 is formed through which the guide wire grasping device 1 can be inserted. The distal end of the channel 103 communicates with an opening 103a provided on the side surface of the distal end of the insertion part 102. An elevating base 104 is attached to the channel 103 formed in the distal end of the insertion part 102. An elevator base operating wire (not shown) extending to the operation part 101 is connected to the elevator base 104.

The operation part 101 is provided with a knob 105 for bending the distal end of the insertion part 102 and a lever 106 for operating the elevator base 104 via an operation wire (not shown). Further, the operation part 101 is connected to a control device (not shown), a display device, a power supply, and the like via a universal cable 107. A forceps plug 108 communicating with the proximal end of the channel 103 is provided on the side portion of the operation part 101. The guide wire grasping device 1 can be inserted into the channel 103 from the forceps plug 108 and projected from the opening 103a.

Next, the guidewire grasping device 1 according to the present embodiment will be described. The guide wire grasping device 1 is a medical instrument used for grasping a known guide wire W. The outer diameter ((i.e., a measurement of the distance of a straight line from one point on the outer wall of the object, through its center, to an opposite point also on the outside) of the guide wire W may be, for example, 0.6 mm or about 0.6 mm. As shown in FIGS. 1 to 7, the guide wire grasping device 1 includes a sheath 10, an operation wire (advanceable and retractable part or linear member) 20, a grasping member (grasping portion) 30, a support part 31, and an operation control (operation part) 40.

The sheath 10 has a central axis extending along the longitudinal axis O1. In the present embodiment, the sheath 10 has a tubular sheath main body 11 extending along the longitudinal axis O1 and a tubular distal end (tubular distal end member) 12 provided at the distal end of the sheath main body 11 along the longitudinal axis O1.

The sheath main body 11 has flexibility and is formed of a suitable resin, such as, for example, PTFE (polytetrafluoroethylene). The sheath main body 11 is a multi-lumen tube having a plurality of lumens. In the present embodiment, the sheath main body 11 has a first lumen 13 and a second lumen 14 extending along the longitudinal axis O1. The first lumen 13 has the largest inner diameter among the plurality of lumens and is opened at the distal end of the sheath main body 11. The first lumen 13 is used for delivery of a contrast medium or the like and for insertion of a guide wire. The second lumen 14 has an inner diameter smaller than the inner diameter of the first lumen 13 and is opened at the distal end of the sheath main body 11. In the second lumen 14, an operation wire 20 is inserted.

The distal end member 12 constitutes the distal end 10a of the sheath 10. The distal end member 12 has higher rigidity than the sheath main body 11, and is formed of a metal such as stainless steel, for example. As shown in FIG. 3, the distal end (distal end member) 12 is fitted and fixed to the distal end of the sheath main body 11. Therefore, the proximal end of the distal end member 12 is positioned within the sheath main body 11. In the tubular distal end (tubular distal end member) 12, both ends of the internal space 15 are open. The inner space 15 has an inner diameter substantially equal to that of the first lumen 13, is arranged coaxially with the first lumen 13, and communicates with the first lumen 13. The outer diameter of the distal end member 12 is set to be smaller than the outer diameter of the sheath main body 11. In the present embodiment, the outer peripheral surface 16 of the distal end member 12 has a flat portion 16a which is a plane parallel to the longitudinal axis O1. The flat portion 16a extends from the distal end to the proximal end of the distal end member 12, and is formed in a rectangular shape. The shortest distance between the two side ends extending from the distal end of the distal end member 12 to the proximal end in the flat portion 16a is set to be larger than the outer diameter of the guide wire W. The flat portion 16a is not necessarily required to extend from the distal end to the proximal end of the distal end member 12. For example, the proximal end of the flat portion 16a may be located more distal than the distal end of the sheath main body 11, and may be positioned closer to the proximal side than the proximal end 30b of the contact surface 30s when the contact surface 30s of the grasping member 30, which will be described later, faces the outer peripheral surface 16 of the distal end member 12 (when grasping the guide wire W). Further, the flat portion 16a is not necessarily rectangular, and may be any shape as long as it has a surface capable of grasping the guide wire W, such as a circular shape, an elliptic shape, an oval shape, a fan shape, or the like.

The operation wire 20 extends from the proximal end of the sheath 10 to the distal end 10a along the longitudinal axis O1 of the sheath 10. The outer diameter of the operation wire 20 is set to be smaller than the inner diameter of the second lumen 14. The operation wire 20 is inserted into the second lumen 14 so as to be able to advance and retract, and protrudes from the distal end opening of the second lumen 14. As the operation wire 20 or material thereof, a known medical wire or materials therefor may be selected.

The grasping member 30 extends in a direction along the longitudinal axis O1 of the sheath 10, Further, the grasping member 30 has a distal end 30a, a proximal end 30b, and a contact surface 30s whose periphery is surrounded by a pair of side ends 30c, 30d extending between the distal end 30a and the proximal end 30b. In the following description, one of the pair of side ends 30c and 30d is appropriately referred to as a first side end 30c and the other is referred to as a second side end 30d as appropriate. The support part 31 is connected to the distal end of the operation wire 20 and fixed to the first side end 30c of the contact surface 30s.

In the present embodiment, the support part 31 is disposed outside the distal end member 12. The support part 31 is attached to the distal end member 12 so as to be rotatable with respect to the distal end member 12 around an axis O2 parallel to a direction substantially orthogonal to the longitudinal axis O1. The support part 31 has a support part main body 32 and a coupling portion 33. The support part main body 32 is formed in a rod shape and has a first end portion 32a and a second end portion 32b opposite to the first end portion 32a. The first end portion 32a is bent substantially at a right angle and inserted into the through hole 12h formed in the distal end member 12. The through hole 12h penetrates from the outer peripheral surface 16 of the distal end member 12 to the inner space 15, and is a hole having the axis O2 as the central axis. The distal end of the first end portion 32a inserted into the through hole 12h is prevented from coming out by known means such as caulking. The first end portion 32a inserted into the through hole 12h functions as a pivot axis in the pivoting motion of the support part 31 around the axis O2. The second end portion 32b is fixed to the grasping member 30. The coupling portion 33 is formed in a bar shape having an outer diameter substantially equal to the outer diameter of the operating wire 20. One end of the coupling portion 33 is fixed to the distal end of the operating wire 20 by a known means such as welding. The other end of the coupling portion 33 is connected to the intermediate portion 32c between the first end portion 32a and the second end portion 32b in the support part main body 32, rotatable about an axis parallel to the axis O2 via a known pin. With such a configuration, the support part 31 is rotated with respect to the distal end member 12 around the axis O2 in accordance with the advancing and retracting motion of the operation wire 20.

In the contact surface 30s of the grasping member 30, the distal end 30a is the distal end side in the direction along the longitudinal axis O1. The proximal end 30b is the opposite end of the distal end 30a. The first side end 30c is an end fixed to the support part 31 among the ends extending from the distal end 30a to the proximal end 30b, more specifically, an end fixed to the second end portion 32b of the support part main body 32. The second side end 30d is an end opposite to the first side end 30c. In the present embodiment, the grasping member 30 is formed in a flat plate shape. The contact surface 30s is provided so as to face the flat portion 16a of the distal end member 12 when grasping the guide wire W.

Like the distal end member 12, the grasping member 30 is formed of a metal material such as stainless steel or the like.

As shown in FIGS. 3 and 6, the grasping member 30 can relatively move with respect to the distal end 10*a* of the sheath 10 so that the distance between the contact surface 30*s* and the outer peripheral surface of the distal end 10*a* of the sheath 10 changes. In the present embodiment, since the distal end 10*a* of the sheath 10 is constituted by the distal end member 12, the grasping member 30 can relatively move with respect to the distal end member 12 so that the distance between the contact surface 30*s* and the outer peripheral surface 16 of the distal end member 12 changes.

The gap between the contact surface 30*s* of the grasping member 30 and the outer peripheral surface 16 of the distal end member 12 is opened at the distal end 30*a*, the proximal end 30*b*, and the second side end 30*d* of the contact surface 30*s*, so that the guide wire W is accommodated in the gap from the second side end 30*d* of the contact surface 30*s* or the guide wire W is released from the gap. With such a configuration, the guide wire W can be inserted between the contact surface 30*s* and the outer peripheral surface 16 from the second side end 30*d* side, and the guide wire W can be disposed between the contact surface 30*s* and the outer peripheral surface 16 in parallel with the longitudinal axis O1 so as to protrude from the distal end 30*a* and the proximal end 30*b* of the contact surface 30*s*, respectively.

The guide wire W disposed in the gap between the contact surface 30*s* and the outer peripheral surface 16 moves the grasping member 30 to a position facing the outer peripheral surface 16 according to the movement of the operation wire 20 and the support part 31, thereby the operation wire 20 (or any other item that may be accommodated between the contact surface and the outer peripheral surface) is grasped (which may occur in a such a manner so that little or no slipping of the operation wire 20 or item disposed between the contact surface and the outer peripheral surface occur with the operation wire 20 or item is effectively grasped) between the contact surface 30*s* and the outer peripheral surface 16.

More specifically, the grasping member 30 is configured to be movable between a first position and a second position. When the grasping member (grasping portion) 30 is in the first position, for example, as shown in FIG. 6, the contact surface 30*s* and the outer peripheral surface 16 are separated from each other. When the grasping member (grasping portion) 30 is in the second position, for example, as shown in FIG. 3, the contact surface 30*s* and the outer peripheral surface 16 are closer to each other than the positional relationship between the contact surface 30*s* and the outer peripheral surface 16 when the grasping member 30 is in the first position. The grasping member 30 is configured to move between the first position and the second position by the support part 31 rotating with respect to the distal end member 12 in accordance with the relative movement of the operation wire 20 with respect to the sheath 10. Specifically, in the second position shown in FIG. 3, when the operation wire 20 is moved (advanced) toward the distal end side along the longitudinal axis O1 with respect to the sheath main body 11, the support part main body 32 is rotated with respect to the distal end member 12 via the coupling portion 33 of the support part 31 so that the support part main body 32 is directed toward the distal end side from the axis O2 around the axis O2 as a center. The grasping member 30 fixed to the second end portion 32*b* accompanying the rotating motion of the support part main body 32 is simultaneously rotated with respect to the distal end member 12 so as to be directed toward the distal end side from the axis O2 around the axis O2 as a center. Thereby, the grasping member (grasping portion) 30 moves from the second position shown in FIG. 3 to the first position shown in FIG. 6. At the first position Shown in FIG. 6, when the operation wire 20 is moved (retracted) toward the proximal end side along the longitudinal axis O1 with respect to the sheath main body 11, the support part main body 32 is rotated relative to the distal end member 12 via the coupling portion 33 of the support part 31 so that the support portion main body 32 is directed toward the proximal end side from the axial line O2 around the axis O2 as a center. The grasping member 30 fixed to the second end portion 32*b* accompanying the rotating motion of the support part main body 32 is simultaneously rotated about the axis O2 toward the proximal end side of the axis O2 with respect to the distal end member 12. Thereby, the grasping member (grasping portion) 30 moves from the first position shown in FIG. 6 to the second position shown in FIG. 3.

When the grasping member 30 is in the first position, the distance between the contact surface 30*s* and the distal end member 12 is larger than the outer diameter of the guide wire W. Therefore, it is possible to easily insert the guide wire W between the contact surface 30*s* and the outer peripheral surface 16 of the distal end member 12.

When the grasping member 30 is in the second position, the guide wire W is grasped between the contact surface 30*s* and the outer peripheral surface 16. In the present embodiment, the guide wire W is sandwiched between the contact surface 30*s* and the flat portion 16*a* of the outer peripheral surface 16, Further, when the grasping member 30 is in the second position, the distance between the contact surface 30*s* and the outer peripheral surface 16 is equal to or smaller than the outer diameter of the guide wire W. Therefore, when the guide wire W is inserted between the contact surface 30*s* and the outer peripheral surface 16, the guide wire W can be surely grasped by the contact surface 30*s* and the outer peripheral surface 16.

The operation control 40 is provided at the proximal end of the operation wire 20, and moves the operation wire 20 along the longitudinal axis O1 of the sheath 10. In the present embodiment, the operation control 40 is provided at the proximal end of the sheath main body 11. As shown in FIG. 7, the operation control (operation part 40) includes an operation control (operation part) main body 41 attached to a proximal end of the sheath main body 11, a bar-shaped handle 42 attached to the operation control (operation part) main body 41, and a slider 43 slideably attached to the handle 42.

A mouthpiece 44 communicating with the first lumen 13 is provided in the operation control main body 41. A finger hook ring 42*a* is attached to the proximal end of the handle 42. A pair of fingering rings 43*a*, 43*a* are attached to the slider 43 so as to sandwich the handle 42 therebetween. The proximal end of the operation wire 20 through which the second lumen 14 is inserted is fixed to the slider 43, and the operation wire 20 can be advanced and retracted along the longitudinal axis O1 according to the movement of the slider 43. Specifically, by moving the slider 43 toward the proximal end with respect to the handle 42, the operation wire 20 is moved (retracted) to the proximal end side along the longitudinal axis O1, and the operation wire 20 moves (advances) toward the distal side along the longitudinal axis O1 by the slider 43 moving to the distal end side relative to the handle 42. Therefore, by moving the slider 43 back and forth with respect to the handle 42, the grasping member 30 can be rotated with respect to the distal end member 12 about the axis O2 as a center.

Figure 8:
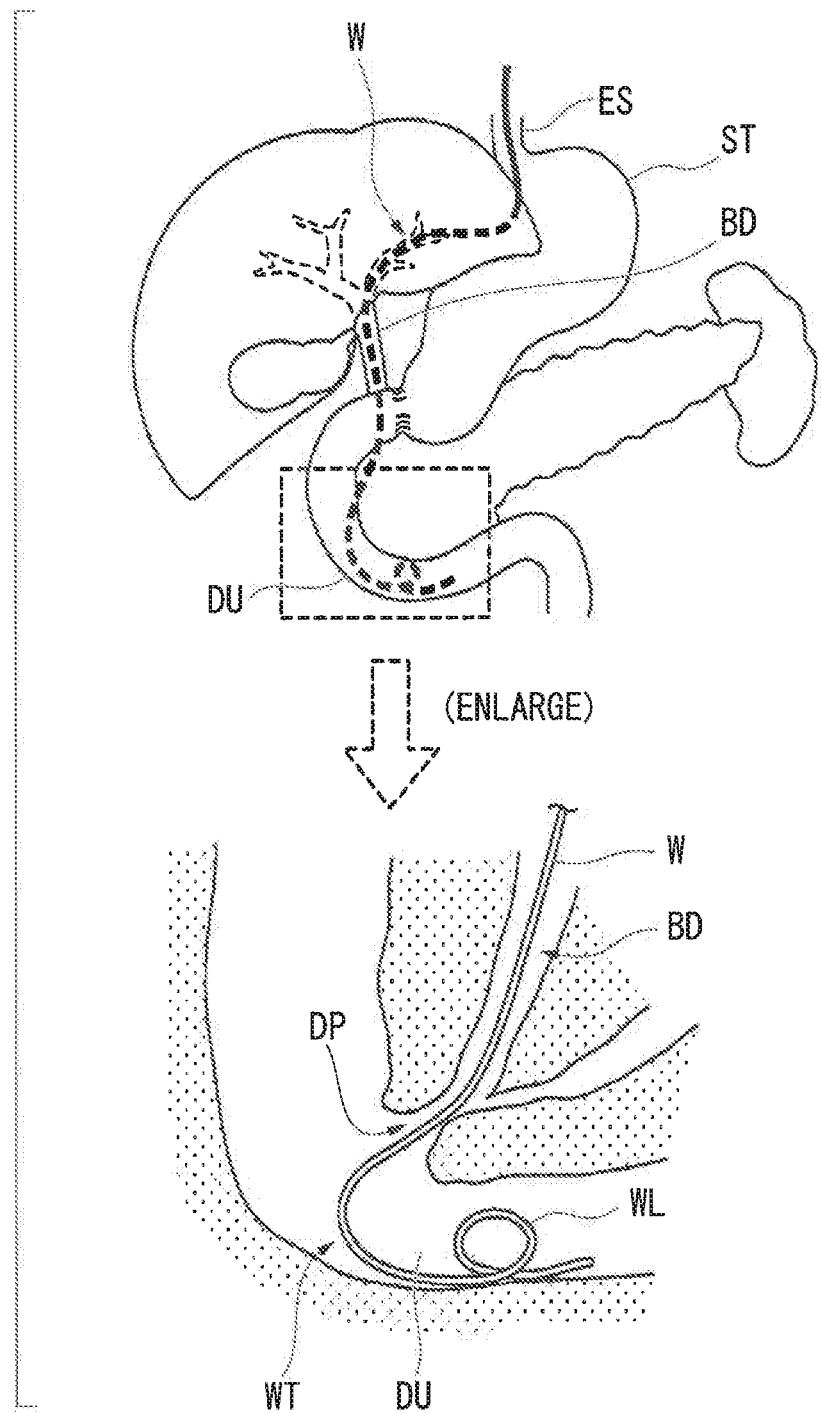
FIG. 8 is a view explaining a procedure using the guide wire grasping device.
Figure 9:
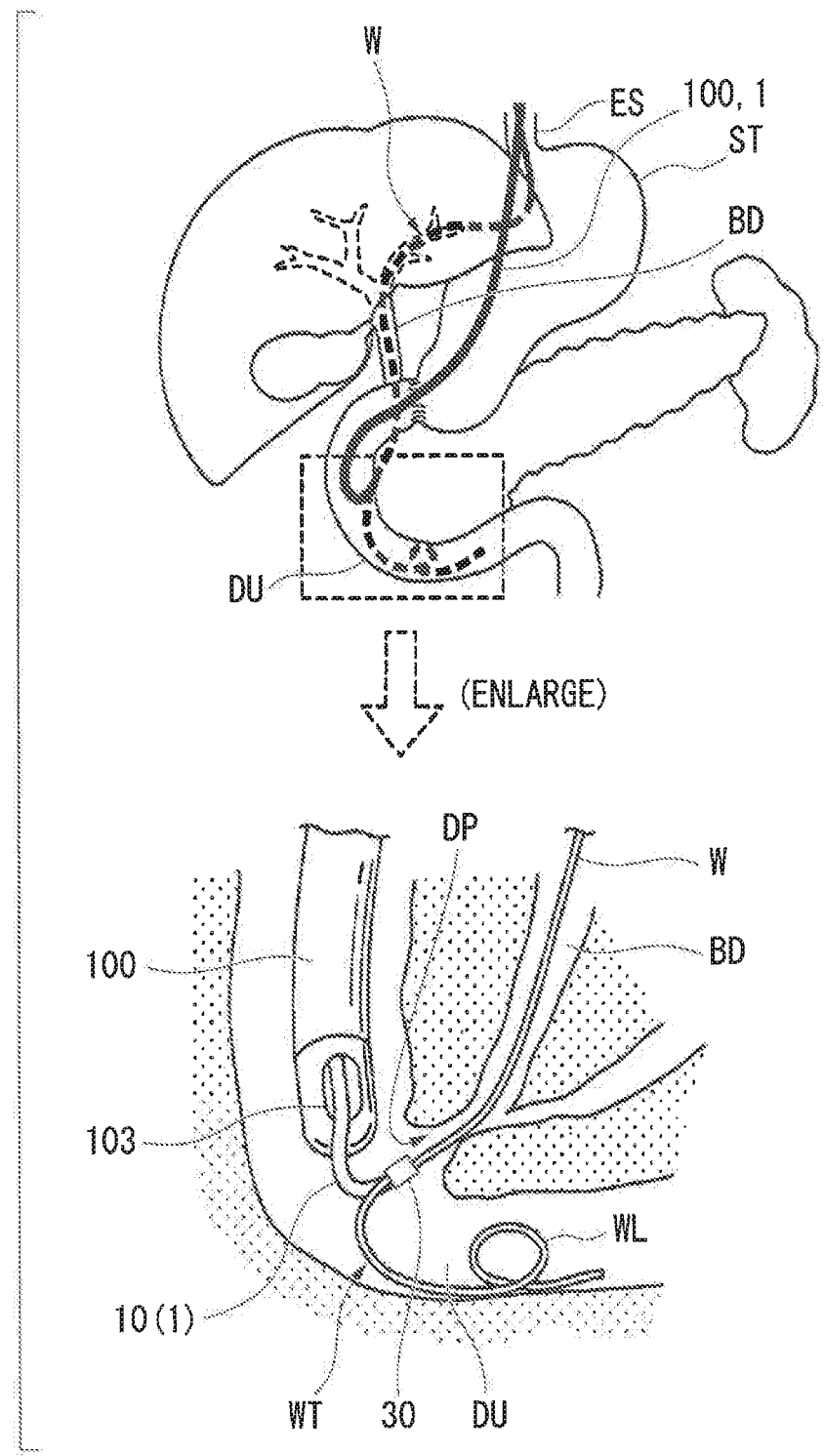
FIG. 9 is a view explaining a procedure using the guide wire grasping device.
Figure 10:
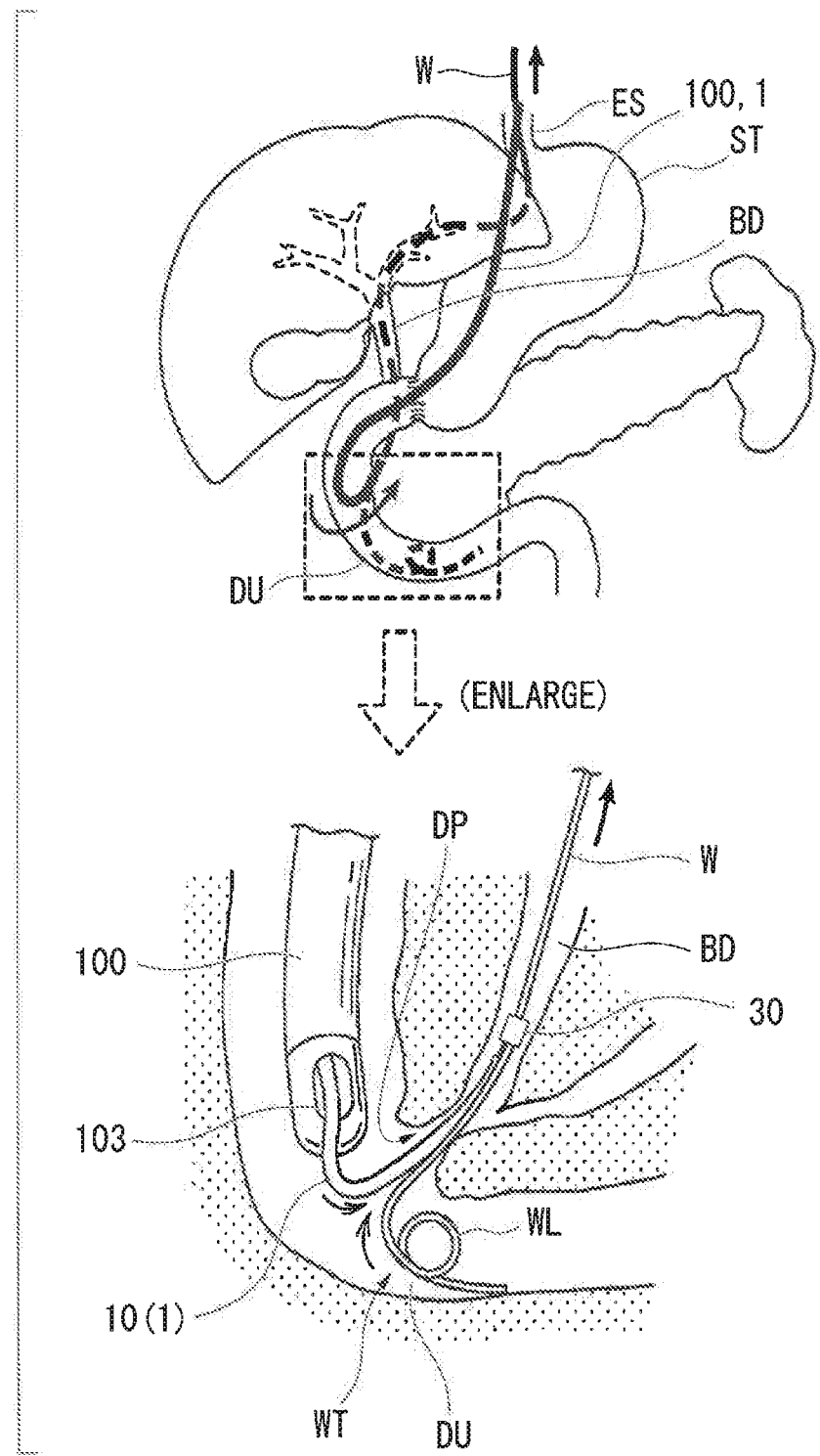
FIG. 10 is a view explaining a procedure using the guide wire grasping device.

Next, an exemplary method of using the guide wire grasping device 1 configured as described above will be described. In the following, as an example, the case where the guide wire grasping device 1 is inserted into the bile duct using the rendezvous method will be described with reference to FIGS. 2, 3, 6, and 8 to 10. FIGS. 8 to 10 are diagrams explaining a procedure using the guide wire grasping device 1.

First, the surgeon inserts a known ultrasonic endoscope into the digestive tract from the patient's mouth. Next, the bile duct BD is confirmed with the ultrasonic image, and a puncture needle inserted into the channel of the ultrasonic endoscope is punctured into the intrahepatic bile duct from the esophagus ES or the stomach ST. The guide wire W is inserted into the puncture needle, and the distal end of the guide wire W is inserted from the puncture needle into the bile duct BD. The operator pushes the guide wire W inserted into the bile duct BD and causes the distal end WT of the guide wire W to protrude into the duodenum DU from the duodenal papilla DP as shown in FIG. 8. Normally, when the guide wire W having a predetermined length is protruded from the duodenal papilla DP, the loop WL is formed at the distal end WT of the guide wire W. Thereafter, the ultrasonic endoscope and the puncture needle are pulled out of the body while the distal end WT of the guide wire W is indwelled in the duodenum DU. At this time, the proximal end side of the guide wire W is outside the patient's body.

Next, as shown in FIG. 9, the surgeon inserts the endoscope 100 from the patient's mouth to the vicinity of the duodenal papilla DP of the duodenum DU. The guide wire grasping device 1 is inserted into the channel 103 of the endoscope 100. After the guide wire grasping device 1 protrudes from the channel 103, the grasping member 30 of the guide wire grasping device 1 is moved to the first position. In this state, while confirming the guide wire W protruding from the duodenal papilla DP with the image of the endoscope 100, the guide wire W is arranged between the contact surface 30s of the grasping member (grasping portion) 30 and the outer peripheral surface 16 of the distal end member 12 as shown in FIG. 6. Then, by moving the grasping member 30 to the second position, the guide wire W is grasped by the contact surface 30s and the outer peripheral surface 16 of the distal end member 12 as shown in FIG. 3. At this time, the orientation of the guide wire W is appropriately adjusted so that the axis of the guide wire W and the longitudinal axis O1 of the sheath 10 are substantially parallel at the distal end 10a of the sheath 10.

The surgeon pulls the proximal end side of the guide wire W which is outside the patient's body toward the outside of the body. As shown in FIG. 10, by this operation, the guide wire W protruding into the duodenum DU is drawn into the bile duct BD from the duodenal papilla DP. Along with the operation of the guide wire W, the guide wire grasping device 1 holding the guide wire W is also drawn into the bile duct BD from the duodenal papilla DP. At this time, the axis of the guide wire W and the longitudinal axis O1 of the sheath 10 are substantially parallel to each other at the distal end 10a of the sheath 10 of the guide wire grasping device 1. Therefore, the guide wire grasping device 1 smoothly advances from the duodenal papilla DP together with the guide wire W into the bile duct BD.

Thereafter, predetermined treatment is performed, for example, by introducing the contrast medium into the bile duct BD through the first lumen 13 of the guidewire grasping device 1.

According to the present embodiment, a guide wire grasping device 1 includes: a sheath 10 having a central axis extending along a longitudinal axis O1; an operation wire 20 extending along the longitudinal axis O1 from a proximal end of the sheath 10 to a distal end 10a of the sheath 10; an operation control (operation part) 40 that is provided at a proximal end of the operation wire 20 and moves the operation wire 20 along the longitudinal axis O1; a grasping member 30 having a contact surface 30s having a peripheral edge surrounded by a distal end 30a, a proximal end 30b, and a first side end 30c and a second side end 30d extending between the distal end 30 a and the proximal end 30b, and extending in a direction along the longitudinal axis O1; and a support part 31 connected to a distal end of the operation wire 20 and fixed to the first side end 30c. A gap between the contact surface 30s and an outer peripheral surface 16 of the distal end 10a of the sheath 10 is open at the distal end 30a, the proximal end 30b, and the second side end 30d of the contact surface 30s so that the guide wire W is accommodated in the gap from the second side end 30d or the guide wire W is released from the gap. The grasping member 30 is moved to a position facing the outer peripheral surface 16 according to a movement of the operation wire 20 and the support part 31, whereby the guide wire W disposed in the gap is grasped between the contact surface 30s and the outer peripheral surface 16.

According to such a configuration, the gap between the contact surface 30s and the outer peripheral surface 16 of the distal end 10a of the sheath 10 is open at the distal end 30a, the proximal end 30b, and the second side end 30d of the contact surface 30s as described above, so the guide wire W can be inserted between the contact surface 30s and the distal end 10a of the sheath 10 from the side of the second side end 30d. Further, the guide wire W can be arranged between the contact surface 30s and the distal end 10a of the sheath 10 in parallel with the longitudinal axis O1 so as to protrude from the distal end 30a and the proximal end 30b of the contact surface 30s, respectively. After disposing the guide wire W in this way, by moving the grasping member 30 to a position opposed to the outer peripheral surface 16, the guide wire W can be grasped in parallel with the longitudinal axis O1 between the contact surface 30s and the outer peripheral surface 16. Therefore, when the guide wire W grasped by the guide wire grasping device 1 is drawn from the duodenal papilla DP into the bile duct BD from the duodenal papilla DP, for example, the guide wire grasping device 1 can be easily introduced into the bile duct BD together with the guide wire W.

The grasping member 30 is movable between a first position where the distance between the contact surface 30s and the distal end 10a of the sheath 10 is larger than the outer diameter of the guide wire W and a second position where the distance between the contact surface 30s and the outer peripheral surface 16 is equal to or less than the outer diameter of the guide wire W. Therefore, when the grasping member 30 is in the first position, the guide wire W can be easily inserted between the contact surface 30s and the distal end 10a of the sheath 10. Further, in the case where the grasping member 30 is in the second position, when the guide wire W is inserted between the contact surface 30s and the outer peripheral surface 16, the guide wire W can be reliably grasped by the contact surface 30s and the outer peripheral surface 16.

The outer peripheral surface 16 has a flat portion 16a which is a plane parallel to the longitudinal axis O1. When the grasping member 30 is in the second position, the guide wire W is sandwiched between the contact surface 30s and the flat portion 16a. According to such a configuration, since the wide wire W in a predetermined range can be sandwiched between the two surfaces of the contact surface 30s and the flat portion 16a, the guidewire W can be reliably grasped by the contact surface 30s and the outer peripheral surface 16.

Further, the sheath 10 includes: a tubular sheath main body 11 extending along the longitudinal axis O1; and a tubular distal end (tubular distal end member) 12 provided at the distal end of the sheath main body 11 along the longitudinal axis O1, having higher rigidity than the sheath main body 11, and constituting a distal end portion 10a of the sheath 10. The support part 31 is attached to the distal end member 12 so as to be rotatable with respect to the distal end member 12 around an axis O2 parallel to a direction substantially orthogonal to the longitudinal axis O1. The grasping member 30 is configured to move between the first position and the second position by the support part 31 rotating with respect to the distal end member 12 in accordance with the relative movement of the operation wire 20 with respect to the sheath 10.

According to such a configuration, since the distal end member 12 has higher rigidity than the sheath main body 11, when the guide wire W is grasped by the contact surface 30s of the grasping member 30 and the outer peripheral surface 16 of the distal end member 12, the guide wire W can be firmly supported. Further, by rotating the support part 31 rotatably attached to the distal end member 12, it is possible to move the grasping member 30 between the first position and the second position, so movement between the first position and the second position can be achieved by a simple configuration. In addition, since the support part 31 can be rotated by moving the operation wire 20 to which the support part 31 is fixed at the distal end with respect to the sheath 10, it is possible to rotate the support part 31 and move the grasping member 30 between the first position and the second position by appropriately operating the operation portion 40 provided at the proximal end of the operation wire 20.

In this embodiment, although not shown, the edge on the distal end side of the distal end member 12, the distal end side edge of the sheath main body 11, and the distal end side edge of the grasping member 30 are chamfered or rounded, respectively. The insertion property of the guide wire grasping device 1 may be further improved by providing a taper at a portion of the outer peripheral surface 16 of the distal end member 12 not opposed to the contact surface 30s of the grasping member 30 such that the outer diameter increases from the distal end toward the proximal end thereof. In addition, the insertion property of the guide wire grasping device 1 may be further improved by forming the coupling portion between the sheath main body 11 and the distal end member 12a into a smooth outer shape without forming a step.

Further, in the present embodiment, the sheath main body 11 has two lumens of the first lumen 13 and the second lumen 14, but the guide wire grasping device of the present disclosure is not limited thereto. The sheath main body 11 may have three or more lumens. For example, the sheath main body 11 may have three lumens: a lumen for feeding liquid, a lumen for a guide wire, and a lumen for the operating wire 20. Although the sheath main body 11 is a multi-lumen tube, it is not limited thereto. For example, the sheath main body 11 may have only the first lumen 13. In this case, the operation wire 20 can be disposed outside the sheath main body 11 along the longitudinal axis O1 using known means without passing through the inside of the sheath main body 11.

Further, in the sheath 10, the sheath main body 11 and the distal end member 12 are made of different members, respectively, but it is not limited thereto. For example, the sheath main body 11 and the distal end member 12 may be integrally formed using a resin. In this case, it is preferable to use a hard resin for the portion corresponding to the distal end member 12.

The contact surface 30s of the grasping member 30 and the flat portion 16a of the outer peripheral surface 16 of the distal end member 12 may be provided with a nonslip surface (for example, by treating the outer peripheral surface via a chemical and/or mechanical process to provide a nonslip surface), or a slip stop member may be provided. With such a configuration, the guide wire W can be grasped more firmly by the contact surface 30s and the outer peripheral surface 16.

In the grasping member 30, edges including the distal end 30a, edges including the proximal end 30b, and edges including the second side end 30d may be chamfered or rounded, respectively. With such a configuration, it is possible to prevent the guide wire W from being damaged by the above-mentioned edge when inserting the guide wire W between the contact surface 30s and the outer peripheral surface 16, and it is possible to prevent the guide wire W from being damaged by the above-mentioned edge during grasping the guide wire W by the contact surface 30s and the outer peripheral surface 16.

In the present embodiment, the first end portion 32a of the support part main body 32 is inserted into the through hole 12h of the distal end member 12 in the support part 31 of the grasping member 30, but the guide wire grasping device of the present disclosure is not limited thereto. For example, a second through hole having the same inner diameter as that of the through hole 12h and having the axis O2 as the central axis may be formed at a position facing the through hole 12h and the internal space 15 along the axis O2 in the distal end member 12, so as to penetrate from the outer peripheral surface 16 to the inner space 15. In this case, the first end portion 32a of the support part main body 32 may be disposed so as to pass through both the through hole 12h and the second through hole. That is, the first end portion 32a of the support part main body 32 may be supported by both the through hole 12h and the second through hole. With such a configuration, it is possible to stabilize the rotation operation of the support part 31 about the axis O2 with the first end portion 32a as the pivot axis more effective than the case where the first end portion 32a of the support part main body 32 is supported only by the through hole 12h. In the present embodiment, the through hole 12h penetrates from the outer peripheral surface 16 of the distal end member 12 to the inner space 15, but, when the thickness of the pipe wall of the distal end member 12 is sufficient, the through hole may be formed so as to penetrate only the tube wall without passing through the inner space 15.

A known ratchet mechanism for fixing the position of the slider 43 with respect to the handle 42 at an arbitrary position may be provided on the handle 42 and the slider 43 of the operation control 40. With such a configuration, for example, in a case in which the guide wire W is grasped by the contact surface 30s and the outer peripheral surface 16 by retracting the operation wire 20, when the slider 43 is fixed to the handle 42 by the ratchet mechanism, even if the operator releases the hand from the operation control 40, the grasping of the guide wire W by the contact surface 30s and the outer peripheral surface 16 is maintained. This makes the operation by the operator easier.

(Modification)

Figure 11:
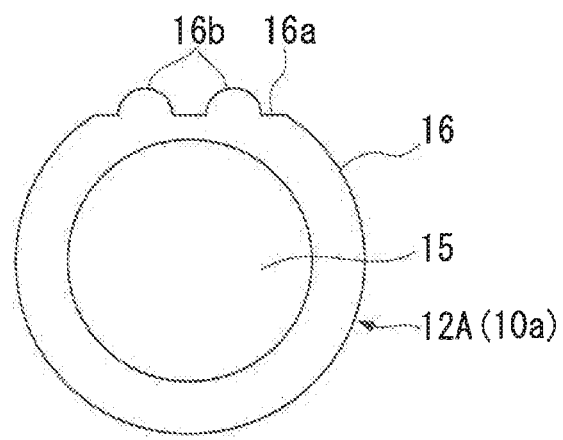
FIG. 11 is a view showing a first modified example of the distal end (distal end member) of the guide wire grasping device.
Figure 12:
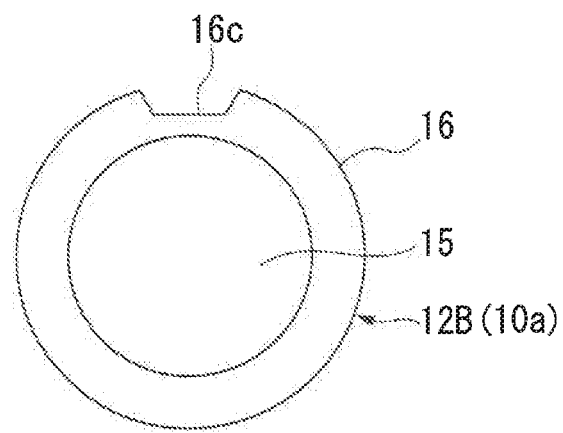
FIG. 12 is a view showing a second modification of the distal end (distal end member).
Figure 13:
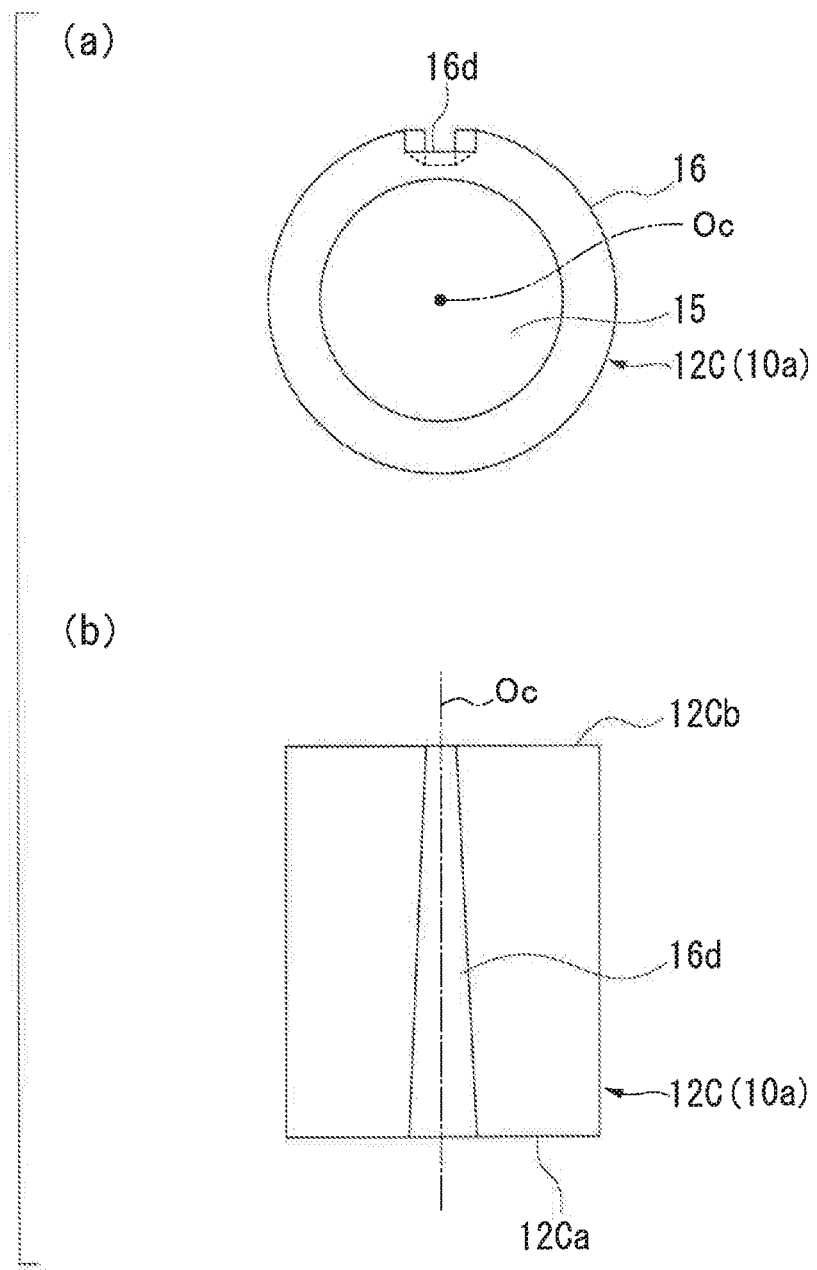
FIG. 13 is a view showing a third modified example of the distal end (distal end member).

In the present embodiment, the outer peripheral surface 16 of the distal end member 12 has the flat portion 16a, but the guide wire grasping device of the present disclosure is not limited thereto. For example, the outer peripheral surface 16 of the distal end member 12 may be configured as in a modified example shown in FIGS. 11 to 13. In FIGS. 11 to 13, for the sake of convenience, components other than the distal end member (for example, sheath main body, grasping member (grasping portion), operation wire, etc.) are omitted.

FIG. 11 is a view showing a first modified example of the distal end member 12. FIG. 11 is a view of the distal end member 12A of the first modification as seen from the distal end side along the longitudinal axis O1. The distal end member 12A is provided with a pair of projections 16b, 16b on the flat portion 16a. The pair of protrusions 16b, 16b are provided along the longitudinal axis O1 so as to protrude from the flat portion 16a, and are arranged to be separated from each other. Each protrusion 16b extends from the distal end to the proximal end of the distal end member 12A. The shape of the cross section perpendicular to the longitudinal axis O1 of each projection 16b is constant along the longitudinal axis O1. Each protrusion 16b is formed in a semicircular shape that becomes convex as it is separated from the flat portion 16a when viewed from a direction along the longitudinal axis O1. The protrusion length protruding from the flat portion 16a of each protrusion 16b is set to be smaller than the outer diameter of the guide wire W. Further, the interval between the pair of protrusions 16b, 16b is set so as to be larger than the outer diameter of the guide wire W, for example. With such a configuration, a space that is recessed with respect to the pair of protrusions 16b, 16b and extends along the longitudinal axis O1 is formed between the pair of protrusions 16b, 16b.

According to such a configuration, when grasping the guide wire W with the contact surface 30s and the outer peripheral surface 16, the movement of the guide wire W is regulated and/or constrained by the pair of projections 16b, 16b, and the pair of projections 16b, 16b. Since the space between the pair of projections 16b, 16b is formed so as to extend along the longitudinal axis O1, the guide wire W is also arranged along the longitudinal axis O1. Therefore, the axis of the guide wire W can easily be made parallel to the longitudinal axis O1, and the guide wire W can be grasped in that state.

FIG. 12 is a view showing a second modification of the distal end member 12. FIG. 12 is a view of the distal end member 12B of the second modification as seen from the distal end side along the longitudinal axis O1. Unlike the distal end member 12, the distal end member 12B has no flat portion 16a on the outer peripheral surface 16, and a concave portion (first concave portion) 16c is formed on the outer peripheral surface 16. The concave portion 16c is recessed in the transverse plane and extends along the longitudinal axis O1. More specifically, the concave portion 16c is formed along the longitudinal axis O1 so as to be recessed with respect to the outer peripheral surface 16. The concave portion 16c extends from the distal end of the distal end member 12B to the proximal end, and the shape of the cross section perpendicular to the longitudinal axis O1 of the concave portion 16c is constant along the longitudinal axis O1. The concave portion 16c has a bottom portion which is a plane parallel to the tangent plane of the outer peripheral surface 16 and a pair of side portions which extend from the bottom portion toward the outer peripheral surface 16. The pair of side portions of the concave portion 16d is inclined with respect to the bottom portion so that the interval between the bottom portion and the outer peripheral surface 16, that is, the opening width becomes larger. The depth of the concave portion 16c (the dimension of the side portion in the direction orthogonal to the bottom portion of the concave portion 16c) is set to be smaller than the outer diameter of the guide wire W. The opening width of the concave portion. 16c is set so as to be larger than the outer diameter of the guide wire W, for example.

According to such a configuration. When grasping the guide wire W with the contact surface 30s and the outer peripheral surface 16 in the case where the grasping member 30 is in the second position, the guide wire W is sandwiched between the contact surface 30s and the concave portion 16c. Since the movement of the guide wire W is regulated and/or constrained by the concave portion 16c, the guide wire W is arranged along the concave portion 16c formed along the longitudinal axis O1. That is, the guide wire W is arranged along the longitudinal axis O1. Therefore, the axis of the guide wire W can easily be made parallel to the longitudinal axis O1, and the guide wire W can be grasped in that state. Further, as described above, since the pair of side portions of the concave portion 16d are inclined, the guide wire W can be easily fitted to the center (an intermediate portion between the pair of side portions) of the concave portion 16d.

The concave portion 16c is not limited to the above shape. For example, the pair of side portions are not inclined with respect to the bottom portion, and the opening width of the concave portion 16c may be constant. In addition, the concave portion 16c may have an integral curved surface by smoothly connecting the bottom portion and a pair of side portions.

FIG. 13 is a view showing a third modified example of the distal end member 12. In FIG. 13, (a) is a view of the distal end member 12C of the third modified example as seen from the distal end side along the longitudinal axis O1, and (b) is a plan view when (a) is a front view of the distal end member 12C. In the distal end member 12C, a concave portion 16d is provided instead of the concave portion 16c of the distal end member 12B of the second modification. The bottom portion of the concave portion 16d is inclined so as to approach the axis Oc of the distal end member 12C from the distal end 12Ca of the distal end member 12C toward the proximal end 12 Cb. In this case, the distance between the bottom portion along one of the pair of side portions of the concave portion 16d in the cross section perpendicular to the longitudinal axis O1 and the outer peripheral surface 16 may increase from the distal end 12Ca toward the proximal end 12Cb. That is, the depth of the concave portion 16d at the distal end 12Ca may be smaller than the depth of the concave portion 16d at the proximal end 12Cb. The pair of side portions of the concave portion 16d are perpendicular to the bottom portion, and are inclined so that the interval therebetween decreases from the distal end 12Ca toward the proximal end 12Cb of the distal end member 12C. Therefore, the opening width of the concave portion 16d at the distal end 12Ca is larger than the opening width of the concave portion 16d at the proximal end 12Cb. The same effect as that of the distal end member 12B of the second modified example described above can be achieved also by the configuration of the distal end member 12C of the third modification.

In the distal end member 12C according to the third modification, the depth of the concave portion 16d at the proximal end 12Cb is larger than the depth of the concave portion 16d at the distal end 12Ca, but the guide wire grasping device of the present disclosure is not limited thereto, and it may be the same as or smaller than the depth of the concave portion 16d at the distal end 12Ca.

Second Embodiment

Figure 14:
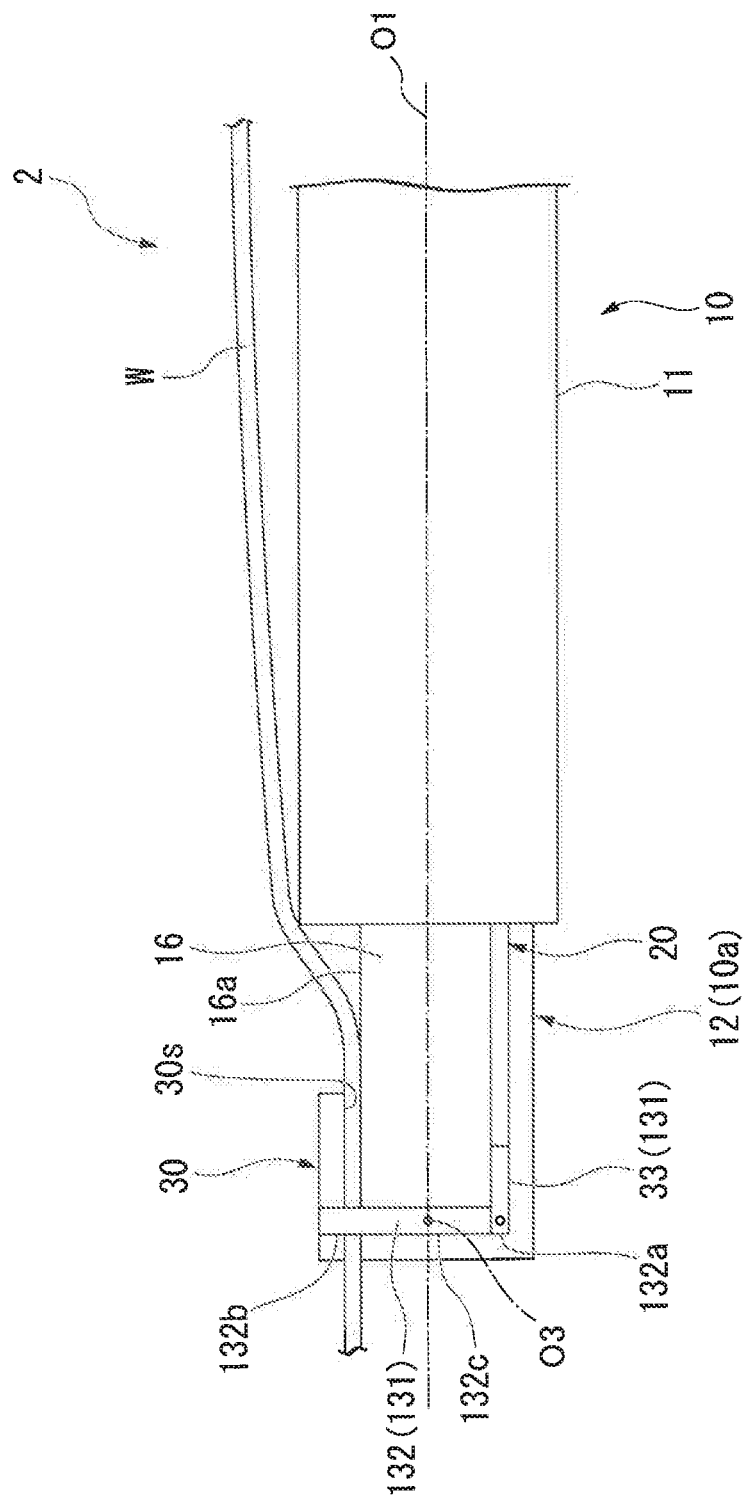
FIG. 14 is a right side view showing the distal end side of the guide wire grasping device according to the second embodiment.
Figure 15:
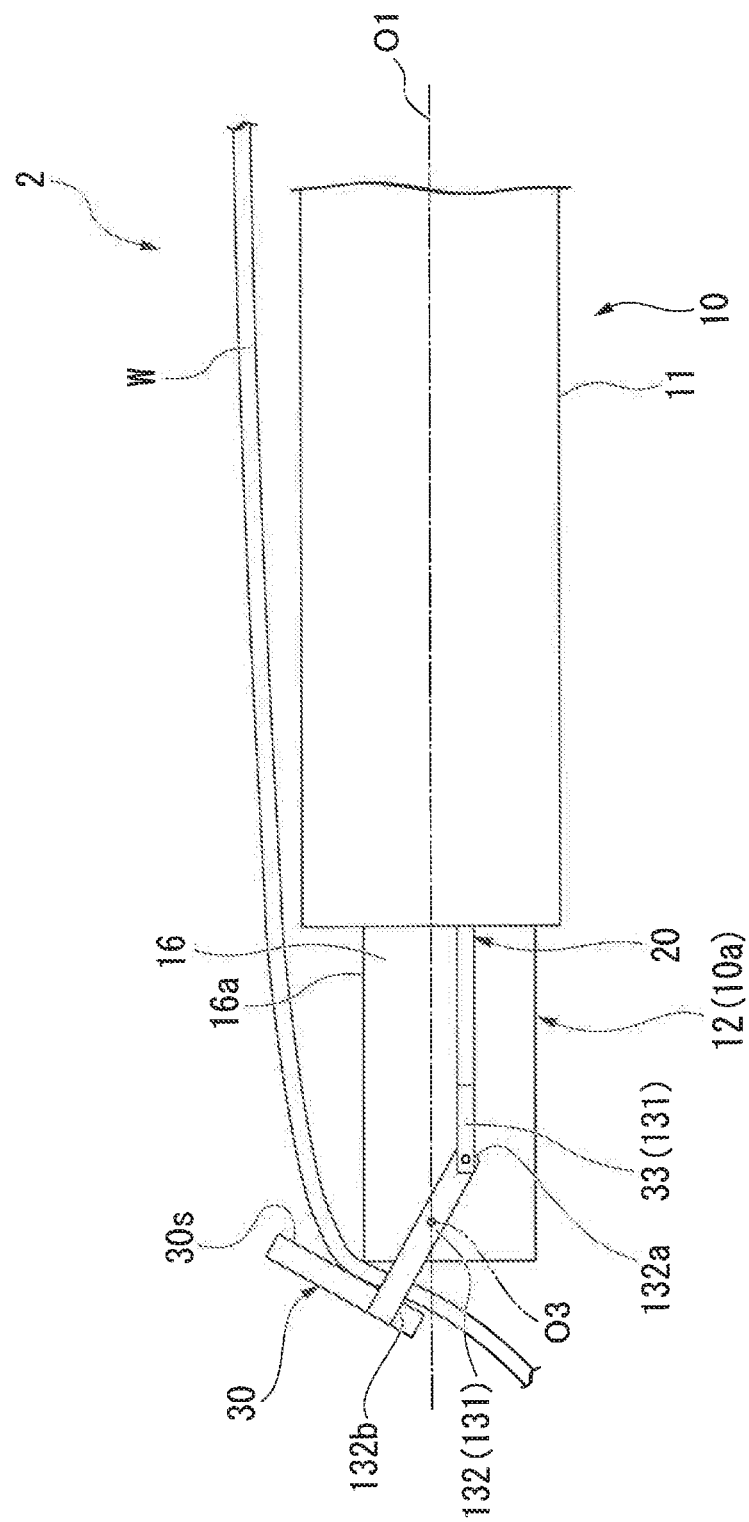
FIG. 15 is a view showing the operation of the grasping member (grasping portion) of the guide wire grasping device.

Next, a second embodiment of the present disclosure will be described with reference to FIGS. 14 and 15. FIG. 14 is a right side view showing the distal end side of the guide wire grasping device 2 according to the present embodiment. FIG. 15 is a view showing the operation of the grasping member (grasping portion) 30 of the guide wire grasping device 2. Note that the same reference numerals are given to parts having the same configuration as the guide wire grasping device 1 according to the first embodiment, and a detailed description thereof will be omitted.

The guide wire grasping device 2 according to the present embodiment is different from the guide wire grasping device 1 according to the first embodiment in the configuration of the support part. The coupling portion 33 is connected to the intermediate portion 32c between the first end portion 32a and the second end portion 32b of the support part main body 32 in the support part 31 of the guide wire grasping device 1, while, in the support part 131 of the guide wire grasping device 2, the position of the coupling portion 33 is different.

In the present embodiment, the support part main body 132 of the support part 131 is formed as a rod like the support part main body 32 according to the first embodiment, and has a first end portion 132a, a second end portion 132b at the opposite side from the first end portion 132a, and a intermediate portion 132c between the first end portion 132a and the second end portion 132b. The second end portion 132b is fixed to the grasping member 30 similarly to the support part main body 32 according to the first embodiment. The intermediate portion 132c is attached to the distal end member 12 so as to be rotatable with respect to the distal end member 12 around an axis O3 parallel to a direction substantially orthogonal to the longitudinal axis O1 via a known pin or the like. The other end of the coupling portion 33 is connected to the first end portion 132a so as to be rotatable about an axis parallel to the axis O3 via a known pin or the like.

With such a configuration, the relationship between the advancing and retracting motion of the operation wire 20 of the guide wire grasping device 2 according to the present embodiment and the pivoting motion of the grasping member 30 is the same as the relationship between the operation wire of the guide wire grasping device 1 according to the first embodiment 20 and the pivotal movement of the grasping member 30. Specifically, as shown in FIG. 14, when the operation wire 20 is retracted along the longitudinal axis O1 with respect to the sheath main body 11 in the case where the grasping member (grasping portion) 30 is in the second position, the grasping member (grasping portion) 30 is rotated with respect to the distal end member 12 about the axis O3 so that the second end portion 132b of the support part main body 132 is directed toward the distal end side from the axis O3 via the coupling portion 33 of the support part 131. As a result, the grasping member (grasping portion) 30 moves from the second position shown in FIG. 14 to the first position shown in 15. As shown in FIG. 15, in the case where the grasping member (grasping portion) 30 is in the first position, when the operation wire 20 is advanced along the longitudinal axis O1 with respect to the sheath main body 11, the grasping member 30 is rotated with respect to the distal end member 12 about the axis O3 so that the second end portion 132b of the support part main body 132 is directed toward the proximal end side from the axis O3 via the coupling portion 33 of the support part 131. As a result, the grasping member 30 moves from the first position shown in FIG. 15 to the second position shown in FIG. 14.

As described above, in the guide wire grasping device 1 according to the first embodiment, the grasping member 30 is moved from the first position to the second position by retracting the operation wire 20, whereas in the guide wire grasping device 2 of the present embodiment, the grasping member 30 is moved from the first position to the second position by advancing the operation wire 20. Normally, the amount of force that can be generated at the distal end of the operation wire 20 is smaller in the case of pushing (advancing) the operation wire 20 than in the case of pulling (retracting) the operation wire 20. Therefore, by configuring as described above, it is possible to reduce the amount of force required for grasping the guide wire W by the contact surface 30s and the outer peripheral surface 16 of the guide wire grasping device 2, as necessary.

Also in the guide wire grasping device 2 according to the present embodiment, the same effect as that of the guide wire grasping device 1 according to the first embodiment can be obtained.

Third Embodiment

Figure 16:
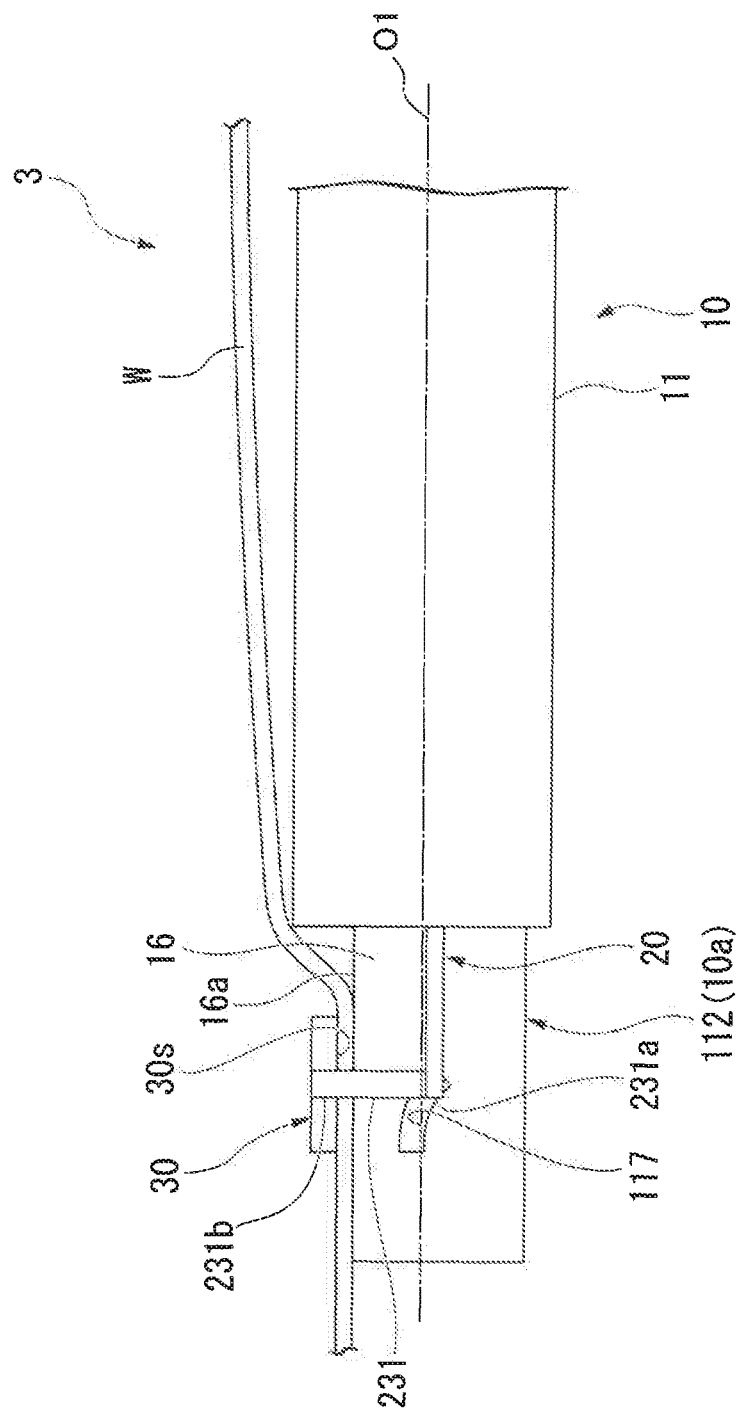
FIG. 16 is a right side view showing the distal end side of the guide wire grasping device according to the third embodiment.
Figure 17:
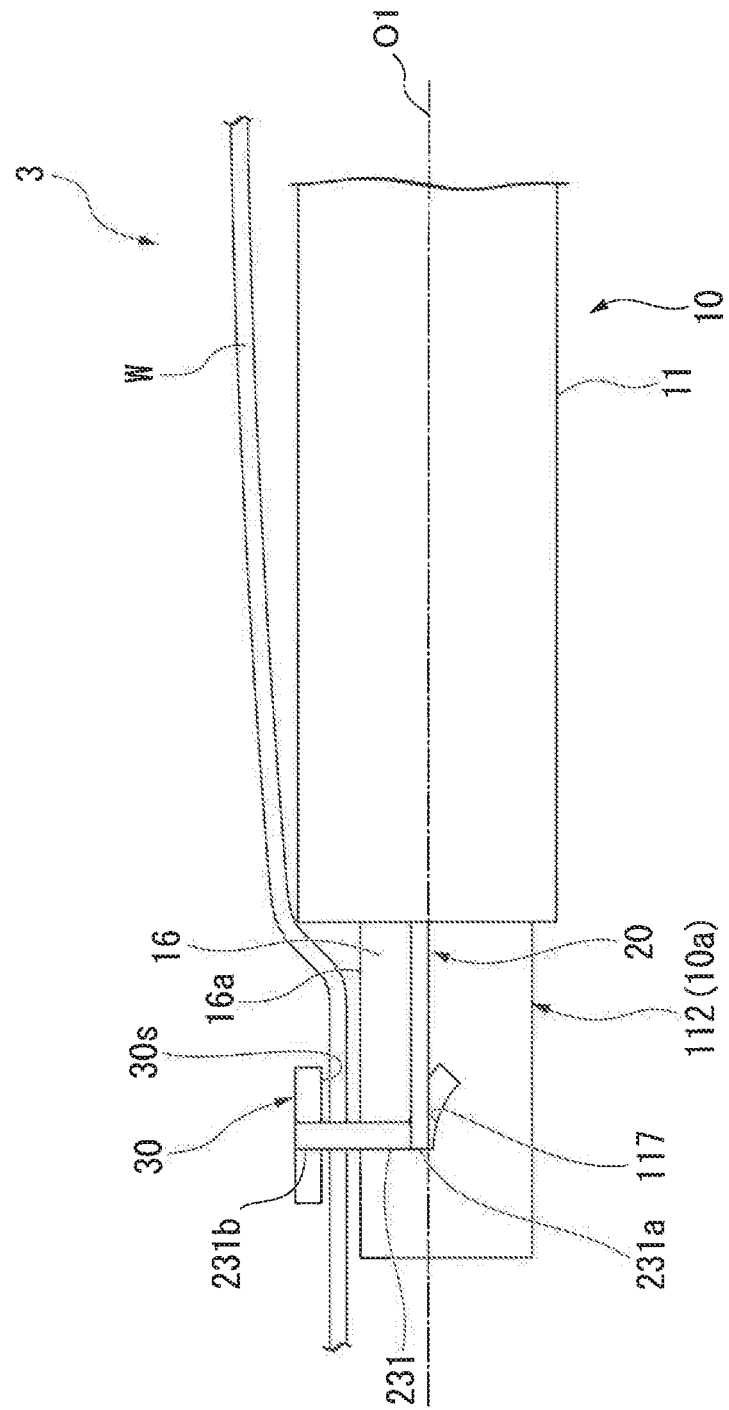
FIG. 17 is a view showing the operation of the grasping member (grasping portion) of the guide wire grasping device.

Next, a third embodiment of the present disclosure will be described with reference to FIGS. 16 and 17. FIG. 16 is a right side view showing the distal end side of the guide wire grasping device 3 according to the present embodiment. FIG. 17 is a view showing the operation of the grasping member 30 of the guide wire grasping device 3. Note that the same reference numerals are given to parts having the same configuration as the guide wire grasping device 1 according to the first embodiment, and a detailed description thereof will be omitted.

The guidewire grasping device 3 according to the present embodiment is different from the guidewire grasping device 1 according to the first embodiment in that the grasping member performs a translational motion relative to the distal end member rather than a rotational motion. In the present embodiment, the support part 231 of the guide wire grasping device 3 is formed like a bar, and has a first end portion 231a and a second end portion 231b on the opposite side from the first end portion 231a. The first end portion 231a is connected to the distal end member 112 so as to be relatively movable with respect to the distal end member 112 of the guide wire grasping device 3. The distal end of the operation wire 20 is fixed to the first end portion 231a by a known means such as welding in such a positional relationship that a substantially right angle is formed between the support part 231 and the distal end of the operation wire. The second end portion 231b is fixed to the grasping member 30 similarly to the second end portion 32b of the support part main body 32 according to the first embodiment. With such a configuration, the operation wire 20 and the grasping member 230 can move relative to the distal end member 112 integrally along the longitudinal axis O1.

The distal end member 112 is different from the distal end member 12 according to the first embodiment in that the distal end member 112 does not have the through hole 12h but has the guide groove 117 instead. The guide groove 117 is formed on the outer peripheral surface 16 of the distal end member 112. In the guide groove 117, the first end portion 231a of the support part 231 of the grasping member 230 is engaged movably in the guide groove 112. The guide groove 117 is formed such that the operation wire 20 and the grasping member 230 move forward and backward relative to the distal end member 112 along the longitudinal axis O1, so that the grasping member (grasping portion) 30 moves between the first position shown in FIG. 17 and the second position shown in FIG. 16.

Specifically, in the present embodiment, the guide groove 117 is formed to penetrate from the outer peripheral surface 16 to the inner space 15. In the guide groove 117, the first end portion 231a of the support part 231 is bent at a substantially right angle and inserted. The distal end of the first end portion 231a inserted into the guide groove 117 is prevented from coming out by known means such as caulking. The guide groove 117 is disposed at a position shifted from the flat portion 16a of the outer peripheral surface 16 by about 90 degrees around the axis of the distal end member 112 when the distal end member 112 is viewed from the distal end side along the longitudinal axis O1. The guide groove 117 is formed in a linear shape extending closer to the flat portion 16a from the proximal end side to the distal end end side. Among such linear shapes, in the present embodiment, the guide groove 117 is formed in a circular arc shape or a curved shape that protrudes toward the flat portion 16a. The width of the guide groove 117 (the dimension in the direction orthogonal to the extending direction in which the guide groove 117 extends on the outer peripheral surface 16) is set so that the first end portion 231a of the support part 231 can move smoothly without any inconvenience along the extending direction of the guide groove 117. As shown in FIG. 16, when the first end portion 231a of the support part 231 is at the proximal end of the guide groove 117, the positional relationship between the contact surface 30s of the grasping member (grasping portion) 30 and the flat portion 16a of the outer peripheral surface 16 is adjusted such that the grasping member (grasping portion) 30 is in the second position.

In the guide wire grasping device 3 configured as described above, in the case where the grasping member (grasping portion) 30 is in the second position shown in FIG. 16, when the operation wire 20 is advanced along the longitudinal axis O1 with respect to the sheath main body 11, the first end portion 231a of the support part 231 fixed to the distal end of the operation wire 20 advances along the guide groove 117 of the outer peripheral surface 16 and moves so as to approach the flat portion 16a of the outer peripheral surface 16. Accordingly, the grasping member 30 fixed to the second end portion 231b of the support part 231 moves so as to be separated from the flat portion 16a. As a result, the grasping member (grasping portion) 30 moves from the second position shown in FIG. 16 to the first position shown in FIG. 17. In the case where the grasping member (grasping portion) 30 is in the first position shown in FIG. 17, when the operation wire 20 is retracted with respect to the sheath main body 11 along the longitudinal axis O1, the first end portion 231a of the support part 231 moves backward along the guide groove 117 and moves away from the flat portion 16a. Accordingly, the grasping member 30 fixed to the second end portion 231b of the support part 231 moves so as to approach the flat portion 16a. As a result, the grasping member (grasping portion) 30 moves from the first position shown in FIG. 17 to the second position shown in FIG. 16. Since the first end portion 231a of the support part 231 is fixed to the distal end of the operation wire 20, when the first end portion 231a moves in the guide groove 117, it is possible to prevent the support part 231 rotating around the first end portion 231a as a center.

Also in the guide wire grasping device 3 according to the present embodiment, the same effect as that of the guide wire grasping device 1 according to the first embodiment can be achieved. In addition, since the grasping member 30 can move from the first position to the second position while maintaining the state in which the contact surface 30s of the grasping member 30 and the flat portion 16a of the outer peripheral surface 16 are substantially parallel, it is possible to grasp the guide wire W more reliably by the planes of the contact surface 30s and the flat portion 16a.

Fourth Embodiment

Figure 18:
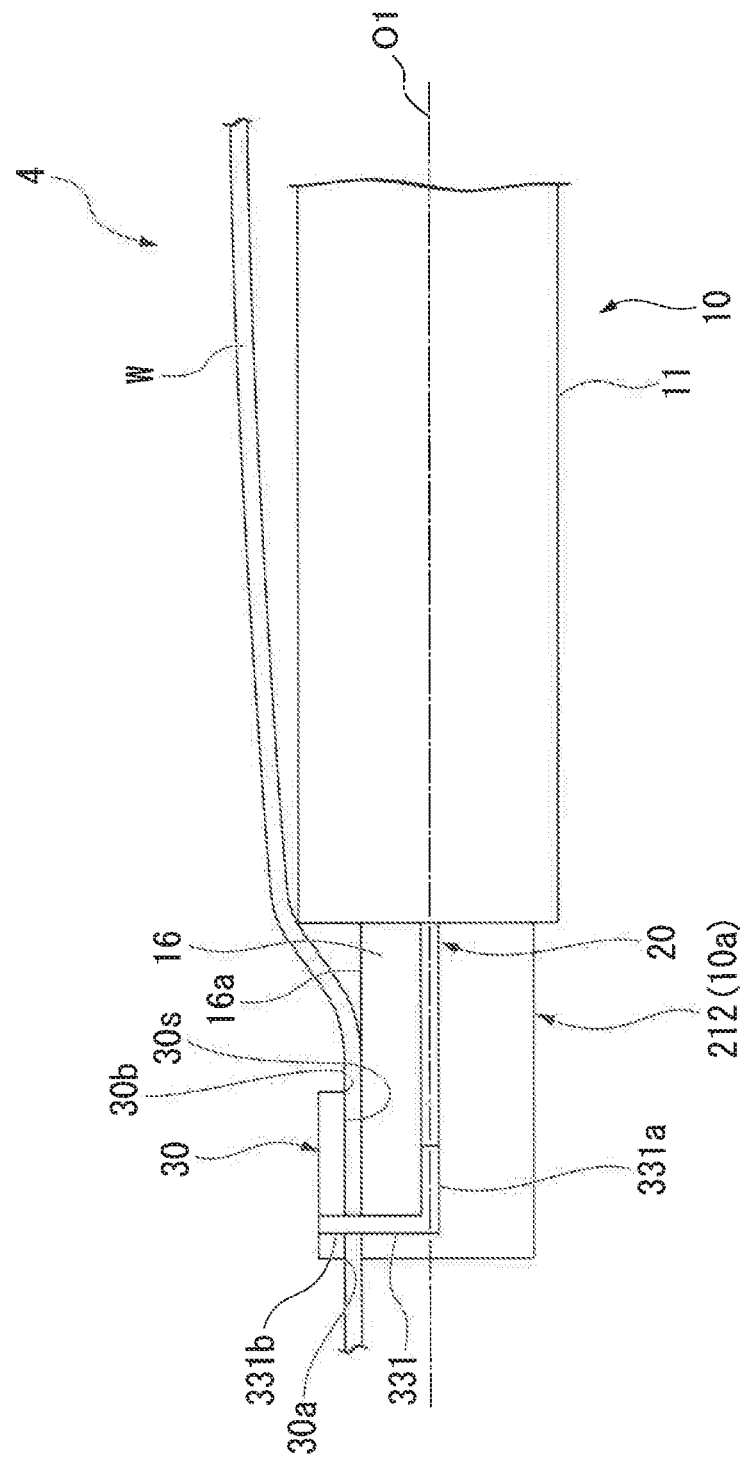
FIG. 18 is a right side view showing the distal end side of the guide wire grasping device according to the fourth embodiment.
Figure 19:
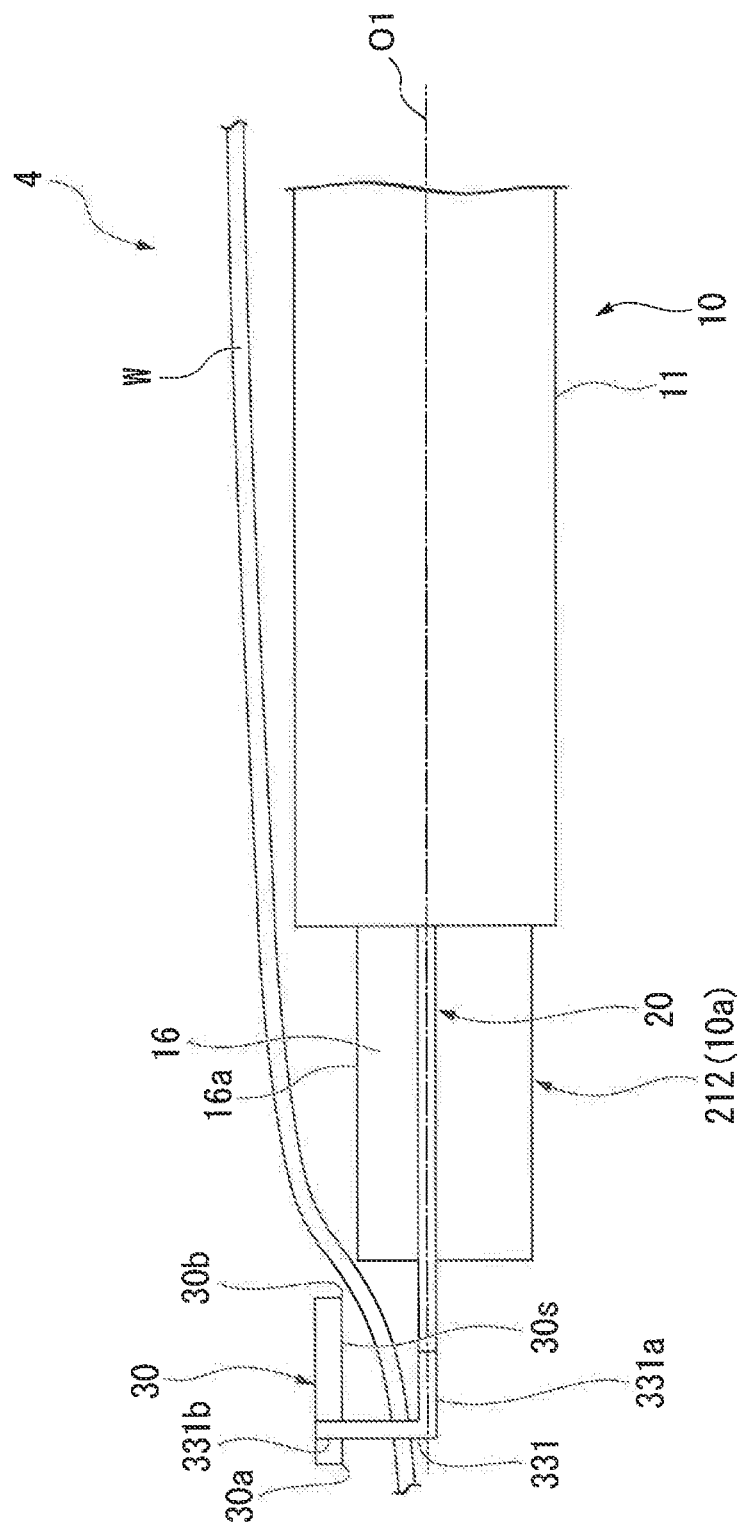
FIG. 19 is a view showing an operation of a grasping member (grasping portion) of the guide wire grasping device.

Next, a fourth embodiment of the present disclosure will be described with reference to FIGS. 18 and 19. FIG. 18 is a right side view showing the distal end side of the guide wire grasping device 4 according to the present embodiment. FIG. 19 is a diagram showing the operation of the grasping member (grasping portion) 30 of the guide wire grasping device 4. Note that the same reference numerals are given to parts having the same configuration as the guide wire grasping device 1 according to the first embodiment, and a detailed description thereof will be omitted.

The guidewire grasping device 4 according to the present embodiment is different from the guidewire grasping device 1 according to the first embodiment in that the grasping member performs a translational motion relative to the distal end member rather than a rotational motion. In the present embodiment, the support part 331 of the guide wire grasping device 4 is formed in an L shape in a bar shape, and has a first end portion 331a and a second end portion 331b on the opposite side from the first end portion 331a. The distal end of the operation wire 20 is fixed to the first end portion 331a by a known means such as welding. The second end portion 331b is fixed to the grasping member 30 similarly to the second end portion 32b of the support part main body 32 according to the first embodiment. Unlike the distal end member 12 according to the first embodiment, the distal end member 212 of the guide wire grasping device 4 does not have the through hole 121h and is not directly connected to the support section 331. With such a configuration, the operating wire 20 and the grasping member 30 can move relative to the distal end member 212 along the longitudinal axis O1.

In addition, the operating wire 20 and the grasping member 30 move forward and backward relative to the distal end member 212 along the longitudinal axis O1, whereby the grasping member (grasping portion) 30 is configured to move between the first position shown in FIG. 19 and the second position shown in FIG. 18. Specifically, in the present embodiment, when the grasping member (grasping portion) 30 is in the second position shown in FIG. 18, the contact surface 30s of the grasping member 30 is arranged to be substantially parallel to the flat portion 16a of the outer peripheral surface 16 of the distal end member 212, The distance between the contact surface 30s and the flat portion 16a is set to be equal to or smaller than the outer diameter of the guide wire W. Thereby, the guide wire W can be grasped by the contact surface 30s and the outer peripheral surface 16. In the case where the grasping member (grasping portion) 30 is in the second position shown in FIG. 18, when the operating wire 20 is advanced along the longitudinal axis O1 with respect to the sheath main body 11, the grasping member (grasping portion) 30 moves along the longitudinal axis O1 together with the operating wire 20. At this time, the grasping member 30 moves forward along the longitudinal axis O1 while maintaining the state in which the contact surface 30s is substantially parallel to the flat portion 16a. When the operating wire 20 is advanced until the distance between the contact surface 30s and the outer peripheral surface 16 becomes large enough to allow insertion of the guide wire W therebetween, more specifically, until the distance between the proximal end 30b of the contact surface 30s and the flat portion 16a becomes larger than the outer diameter of the guide wire W, the grasping member (grasping portion) 30 is moved to the first position shown in FIG. 19. In the case where the grasping member (grasping portion) 30 is in the first position shown in FIG. 19, when the operation wire 20 is retracted along the longitudinal axis O1 with respect to the sheath main body 11, the grasping member (grasping portion) 30 is retracted along the longitudinal axis O1 together with the operation wire 20. At this time, the grasping member 30 is retracted along the longitudinal axis O1 while maintaining the state in which the contact surface 30s is substantially parallel to the flat portion 16a. Thereby, the grasping member (grasping portion) 30 moves from the first position shown in FIG. 19 to the second position shown in FIG. 18.

The guide wire grasping device 4 according to the present embodiment can also achieve the same effect as the guide wire grasping device 1 according to the first embodiment.

Fifth Embodiment

Figure 20:
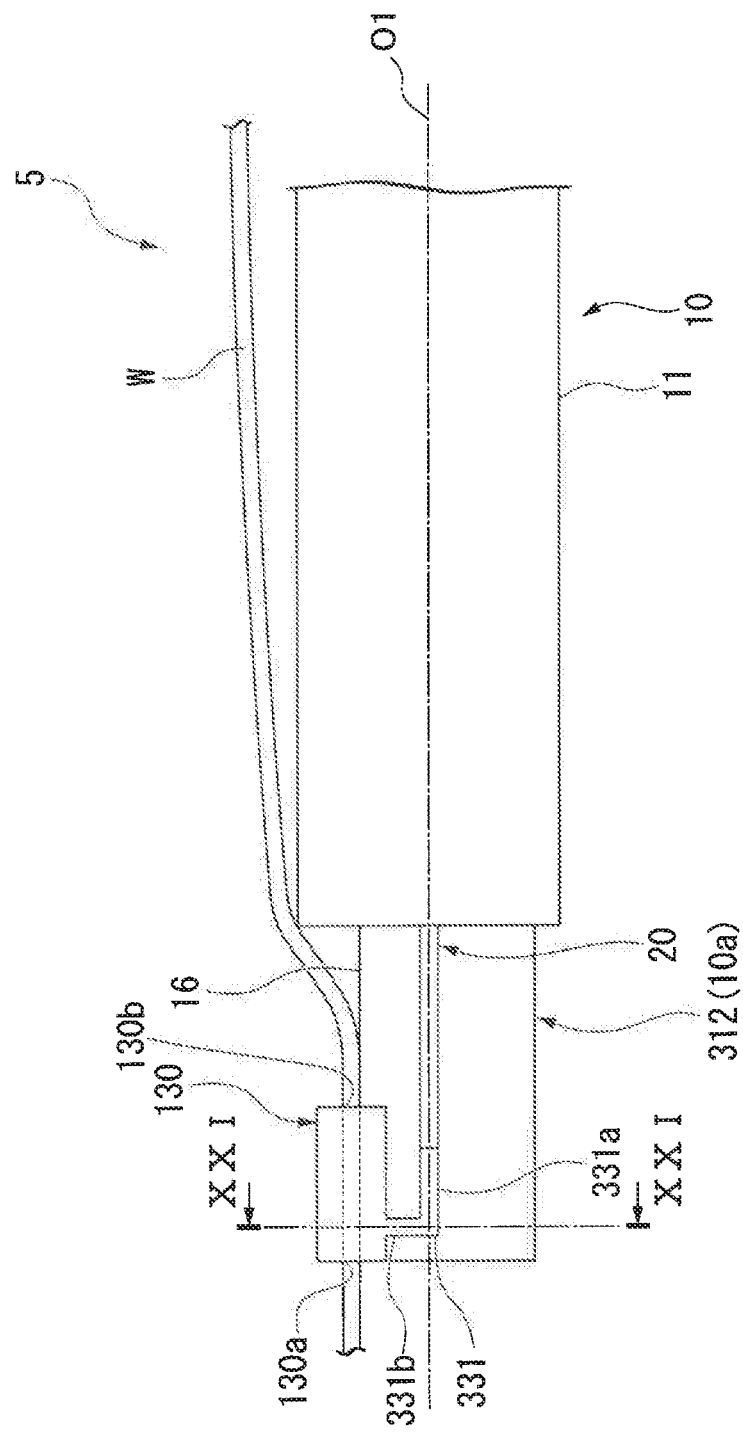
FIG. 20 is a right side view showing the distal end side of the guide wire grasping device according to the fifth embodiment.
Figure 21:
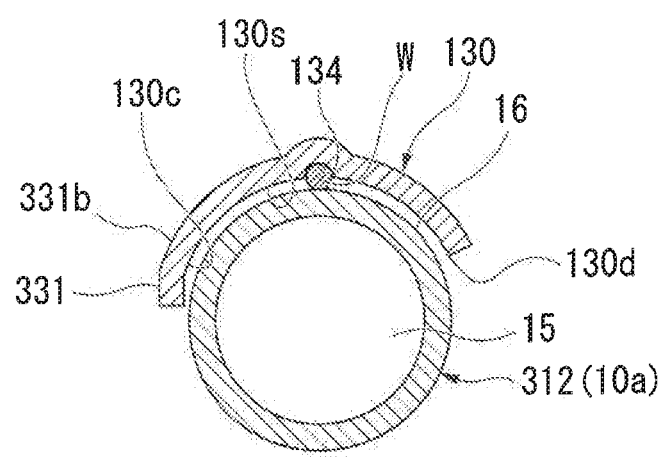
FIG. 21 is a cross-sectional view taken along the line XXI-XXI of FIG. 20.

Next, a fifth embodiment of the present disclosure will be described with reference to FIGS. 20 to 21. FIG. 20 is a right side view showing the distal end side of the guide wire grasping device 5 according to the present embodiment. FIG. 21 is a cross-sectional view taken along line XXI-XXI in FIG. 20. The same reference numerals are given to parts having the same configurations as the guide wire grasping device 1 according to the first embodiment or the guide wire grasping device 4 according to the fourth embodiment, and a detailed description thereof will be omitted.

The guide wire grasping device 5 according to the present embodiment is different from the guide wire grasping device 4 according to the fourth embodiment in the shape of the grasping member. In the present embodiment, the grasping member 130 of the guide wire grasping device 5 is formed in a curved plate shape. Like the grasping member 30 according to the first embodiment, the grasping member 130 has a contact surface 130s whose periphery is surrounded by a distal end 130a, a proximal end 130b, a first side end 130c, and a second side end 130d. The distal end member 312 of the guide wire grasping device 5 is different from the distal end member 212 of the guide wire grasping device 4 according to the fourth embodiment in that the flat portion 16a is not provided on the outer peripheral surface 16. That is, the outer shape of the distal end member 312 as viewed from the direction along the longitudinal axis O1 is circular. As shown in FIG. 21, the grasping member (grasping portion) 130 is curved so as to follow the contour of the distal end member 312 as seen from the direction along the longitudinal axis O1.

Further, as shown in FIG. 21, a concave portion (second concave portion) 134 is provided on the contact surface 130s of the grasping member (grasping portion) 130. The concave portion 134 is recessed in the transverse plane and extends along the longitudinal axis O1. Specifically, the concave portion 134 is formed so as to be recessed with respect to the contact surface 130s along the longitudinal axis O1. The concave portion 134 extends from the distal end 130a to the proximal end 130b of the contact surface 130s, and the shape of the cross section perpendicular to the longitudinal axis O1 of the concave portion 134 is constant along the longitudinal axis O1. The concave portion 134 is formed in a substantially semicircular shape protruding in a direction away from the outer peripheral surface 16 of the distal end member 312 when viewed from a direction along the longitudinal axis O1. The concave portion 134 is set to a size capable of fitting the guidewire W therein.

In the guide wire grasping device 5, the operation of moving the grasping member 130 between the first position and the second position is the same as the operation of the guide wire grasping device 4 according to the fourth embodiment.

According to such a configuration, when the guide wire W is grasped by the contact surface 130s of the grasping member 130 and the outer peripheral surface 16 of the distal end member 312, the guide wire W is sandwiched between the concave portion 134 of the contact surface 130s and the outer peripheral surface 16. Since the movement of the guide wire W is restricted by the concave portion 134, the guide wire W is disposed along the concave portion 134 formed along the longitudinal axis O1. That is, the guide wire W is arranged along the longitudinal axis O1. Therefore, the axis of the guide wire W can easily be made parallel to the longitudinal axis O1, and the guide wire W can be grasped in that state.

Also in the guide wire grasping device 5 according to the present embodiment, the same effect as that of the guide wire grasping device 4 according to the fourth embodiment can be obtained.

It should be noted that the shape of the concave portion 134 as viewed from the direction along the longitudinal axis O1 is not limited to a substantially semicircular shape that protrudes in a direction away from the outer peripheral surface 16 of the distal end member 312. The shape of the concave portion 134 as viewed from the direction along the longitudinal axis O1 may be any arbitrary curved shape which is convex toward the direction away from the outer peripheral surface 16. Further, the shape of the concave portion 134 as seen from the direction along the longitudinal axis O1 may be a triangular shape, a trapezoidal shape or a rectangular shape protruding in a direction away from the outer peripheral surface 16 of the distal end member 312.

In the fourth embodiment and the fifth embodiment described above, the operation wire and the grasping member are moved with respect to the distal end member, but the guide wire grasping device of the present disclosure is not limited thereto. For example, the distal end member may be provided so as to be able to move back and forth along the longitudinal axis with respect to the sheath main body, and the distal end member may be moved with respect to the operation wire and the distal end member whose positions relative to the sheath main body are fixed.

Although preferred embodiments of the present disclosure have been described above, the present disclosure is not limited to these embodiments. Additions, omissions, substitutions, and other changes in the configuration are possible without departing from the spirit of the present disclosure.

According to the embodiments of the present disclosure described above, it is possible to provide a guide wire grasping device which can be easily introduced into a hollow organ by a rendezvous method.

The invention claimed is:

1. A guide wire grasping device, comprising:
   a sheath having a central axis extending along a longitudinal axis;
   an advanceable and retractable part extending along the longitudinal axis from a proximal end of the sheath to a distal end of the sheath;
   an operation control that is provided at a proximal end of the advanceable and retractable part, the operation control being configured to move the advanceable and retractable part along the longitudinal axis;
   a grasping portion having a contact surface having a peripheral edge surrounded by a distal end, a proximal end, and a pair of side ends, the pair of side ends extending between the distal end and the proximal end of the grasping portion, the grasping portion extending in a direction along the longitudinal axis; and
   a support part fixed to one side end of the pair of side ends, wherein:
      at least part of the support part extends between the one side end and a distal end of the advanceable and retractable part in a direction intersecting the longitudinal axis,
      a gap between the contact surface and an outer peripheral surface of the distal end of the sheath is open at the distal end, the proximal end, and the other of the pair of side ends of the contact surface, where the gap is dimensioned to accommodate a guide wire,
      the grasping portion is configured so that the contact surface moves to a position radially outward of the outer peripheral surface of the distal end of the sheath in response to a movement of the advanceable and retractable part and the support part for effectively grasping the guide wire disposed in the gap between the contact surface and the outer peripheral surface, and
      a contact portion of the grasping portion is configured to move between a first position offset in the direction along the longitudinal axis from a position facing the outer peripheral surface and a second position facing the outer peripheral surface.

2. The guide wire grasping device according to claim 1, wherein
   the first position is a position in which a distance between the contact surface and the distal end of the sheath is larger than an outer diameter of the guide wire; and
   the second position is effective to grasp the guide wire disposed in the gap between the contact surface and the outer peripheral surface, the second position being a position in which a distance between the contact surface and the outer peripheral surface is equal to or smaller than the outer diameter of the guide wire.

3. The guide wire grasping device according to claim 2, wherein
   the outer peripheral surface has a flat portion which is a plane parallel to the longitudinal axis, and
   the guide wire is sandwiched between the contact surface and the flat portion when the grasping portion is in the second position.

4. The guide wire grasping device according to claim 2, wherein
   the outer peripheral surface has a first concave portion recessed in a cross section extending along the longitudinal axis, and
   the guide wire is sandwiched between the contact surface and the first concave portion when the grasping portion is in the second position.

5. The guide wire grasping device according to claim 4, wherein
   the first concave portion has a bottom portion and a pair of side portions extending from the bottom portion toward the outer peripheral surface, and
   a distance between the pair of side portions decreases from the distal end to the proximal end of the sheath.

6. The guide wire grasping device according to claim 2, wherein
   the contact surface has a second concave portion recessed in a cross section extending along the longitudinal axis, and
   the guide wire is sandwiched between the second concave portion and the outer peripheral surface when the grasping portion is in the second position.

7. The guide wire grasping device according to claim 2, wherein
   the sheath includes:
      a tubular sheath main body extending along the longitudinal axis, and
      a tubular distal end, which (i) is provided at a distal end of the sheath main body along the longitudinal axis, (ii) has a rigidity higher than that of the sheath main body, and (iii) represents a distal end of the sheath;
   the support part is attached to the tubular distal end so as to be rotatable with respect to the tubular distal end about an axis parallel to a direction substantially orthogonal to the longitudinal axis; and
   the grasping portion is configured to move between the first position and the second position via rotation of the support part relative to the tubular distal end, the support part and the advanceable and retractable part being configured such that movement of the advanceable and retractable part relative to the sheath rotates the support part.

8. The guide wire grasping device according to claim 2, wherein
   the advanceable and retractable part and the grasping portion are configured to move relative to the distal end of the sheath along the longitudinal axis, and
   the grasping portion is configured to move between the first position and the second position via movement of the advanceable and retractable part and the grasping portion in either a forward direction or a backward direction relative to the distal end of the sheath along the longitudinal axis.

9. The guide wire grasping device according to claim 1, wherein
   the outer peripheral surface includes a flat portion which is a plane parallel to the longitudinal axis or a first concave portion recessed in a cross section extending along the longitudinal axis, and
   the contact portion of the grasping portion is configured to face the flat portion or the first concave portion in the second position.

10. The guide wire grasping device according to claim 1, wherein
    at the first position, a dimension of the gap between the contact surface and the outer peripheral surface is larger than an outer diameter of the guide wire; and
    at the second position, the dimension of the gap between the contact surface and the outer peripheral surface is equal to or smaller than the outer diameter of the guide wire.

11. The guide wire grasping device according to claim 9, wherein:
when the contact portion of the grasping portion is in the first position, a dimension of the gap between the flat portion or the first concave portion and the contact surface is larger than an outer diameter of the guide wire, and
when the contact portion of the grasping portion is in the second position, the dimension of the gap between the flat portion or the first concave portion and the contact surface is equal to or smaller than the outer diameter of the guide wire.

12. A guide wire grasping device, comprising:
a sheath having a central axis extending along a longitudinal axis;
an advanceable and retractable part extending along the longitudinal axis from a proximal end of the sheath to a distal end of the sheath;
an operation control that is provided at a proximal end of the advanceable and retractable part, the operation control being configured to move the advanceable and retractable part along the longitudinal axis;
a grasping portion having a contact surface having a peripheral edge surrounded by a distal end, a proximal end, and a pair of side ends, the pair of side ends extending between the distal end and the proximal end of the grasping portion, the grasping portion extending in a direction along the longitudinal axis; and
a support part fixed to one side end of the pair of side ends, wherein:
at least part of the support part extends between the one side end and a distal end of the advanceable and retractable part in a direction intersecting the longitudinal axis,
a gap between the contact surface and an outer peripheral surface of the distal end of the sheath is open at the distal end, the proximal end, and the other of the pair of side ends of the contact surface, where the gap is dimensioned to accommodate a guide wire,
the grasping portion is configured so that the contact surface moves to a position radially outward of the outer peripheral surface of the distal end of the sheath in response to a movement of the advanceable and retractable part and the support part for effectively grasping the guide wire disposed in the gap between the contact surface and the outer peripheral surface,
the outer peripheral surface includes a flat portion which is a plane parallel to the longitudinal axis or a first concave portion recessed in a cross section extending along the longitudinal axis, and
a contact portion of the grasping portion is configured to move to a position facing the flat portion or the first concave portion.

13. The guide wire grasping device according to claim 12, wherein
the grasping portion is movable between a first position and a second position;
the first position is a position in which a distance between the contact surface and the distal end of the sheath is larger than an outer diameter of the guide wire; and
the second position is effective to grasp the guide wire disposed in the gap between the contact surface and the outer peripheral surface, the second position being a position in which a distance between the contact surface and the outer peripheral surface is equal to or smaller than the outer diameter of the guide wire.

14. The guide wire grasping device according to claim 13, wherein
the contact surface has a second concave portion recessed in a cross section extending along the longitudinal axis, and
the guide wire is sandwiched between the second concave portion and the outer peripheral surface when the grasping portion is in the second position.

15. The guide wire grasping device according to claim 13, wherein
the sheath includes:
a tubular sheath main body extending along the longitudinal axis, and
a tubular distal end, which (i) is provided at a distal end of the sheath main body along the longitudinal axis, (ii) has a rigidity higher than that of the sheath main body, and (iii) represents a distal end of the sheath;
the support part is attached to the tubular distal end so as to be rotatable with respect to the tubular distal end about an axis parallel to a direction substantially orthogonal to the longitudinal axis; and
the grasping portion is configured to move between the first position and the second position via rotation of the support part relative to the tubular distal end, the support part and the advanceable and retractable part being configured such that movement of the advanceable and retractable part relative to the sheath rotates the support part.

16. The guide wire grasping device according to claim 13, wherein
the advanceable and retractable part and the grasping portion are configured to move relative to the distal end of the sheath along the longitudinal axis, and
the grasping portion is configured to move between the first position and the second position via movement of the advanceable and retractable part and the grasping portion in either a forward direction or a backward direction relative to the distal end of the sheath along the longitudinal axis.

17. The guide wire grasping device according to claim 12, wherein
the contact portion of the grasping portion is configured to move between a first position offset in the direction along the longitudinal axis from a position facing the outer peripheral surface and a second position facing the outer peripheral surface.

18. The guide wire grasping device according to claim 17, wherein
at the first position, a dimension of the gap between the contact surface and the outer peripheral surface is larger than an outer diameter of the guide wire; and
at the second position, the dimension of the gap between the contact surface and the outer peripheral surface is equal to or smaller than the outer diameter of the guide wire.

19. The guide wire grasping device according to claim 17, wherein:
when the contact portion of the grasping portion is in the first position, a dimension of a gap between the flat portion or the first concave portion and the contact surface is larger than an outer diameter of the guide wire, and
when the contact portion of the grasping portion is in the second position, the dimension of the gap between the flat portion or the first concave portion and the contact surface is equal to or smaller than the outer diameter of the guide wire.

20. A guide wire grasping device, comprising:
a sheath having a central axis extending along a longitudinal axis;
an advanceable and retractable part extending along the longitudinal axis from a proximal end of the sheath to a distal end of the sheath;
an operation control that is provided at a proximal end of the advanceable and retractable part, the operation control being configured to move the advanceable and retractable part along the longitudinal axis;
a grasping portion having a contact surface having a peripheral edge surrounded by a distal end, a proximal end, and a pair of side ends, the pair of side ends extending between the distal end and the proximal end of the grasping portion, the grasping portion extending in a direction along the longitudinal axis; and
a support part fixed to one side end of the pair of side ends, wherein:
  at least part of the support part extends between the one side end and a distal end of the advanceable and retractable part in a direction intersecting the longitudinal axis,
  a gap between the contact surface and an outer peripheral surface of the distal end of the sheath is open at the distal end, the proximal end, and the other of the pair of side ends of the contact surface, where the gap is dimensioned to accommodate a guide wire,
  the grasping portion is configured so that the contact surface moves to a position radially outward of the outer peripheral surface of the distal end of the sheath in response to a movement of the advanceable and retractable part and the support part for effectively grasping the guide wire disposed in the gap between the contact surface and the outer peripheral surface,
  the grasping portion is movable between a first position and a second position,
  the first position is a position in which a distance between the contact surface and the distal end of the sheath is larger than an outer diameter of the guide wire,
  the second position is effective to grasp the guide wire disposed in the gap between the contact surface and the outer peripheral surface, the second position being a position in which a distance between the contact surface and the outer peripheral surface is equal to or smaller than the outer diameter of the guide wire,
  the sheath includes:
    a tubular sheath main body extending along the longitudinal axis, and
    a tubular distal end, which is provided at a distal end of the sheath main body along the longitudinal axis,
  the support part is attached to the tubular distal end so as to be rotatable with respect to the tubular distal end about an axis parallel to a direction substantially orthogonal to the longitudinal axis, and
  the grasping portion is configured to move between the first position and the second position via rotation of the support part relative to the tubular distal end, the support part and the advanceable and retractable part being configured such that movement of the advanceable and retractable part relative to the sheath rotates the support part.

* * * * *